(12) United States Patent
Ealovega et al.

(10) Patent No.: US 11,612,382 B2
(45) Date of Patent: Mar. 28, 2023

(54) FEMALE URINARY DIAGNOSTIC DEVICE

(71) Applicants: George Ealovega, Sebastian, FL (US); Elizabeth Hatz, Port St. Lucie, FL (US)

(72) Inventors: George Ealovega, Sebastian, FL (US); Elizabeth Hatz, Port St. Lucie, FL (US)

(73) Assignee: GLR Medical Innovations LLC, Sebastian, FL (US)

( * ) Notice: Subject to any disclaimer, the term of this patent is extended or adjusted under 35 U.S.C. 154(b) by 69 days.

(21) Appl. No.: 16/857,489

(22) Filed: Apr. 24, 2020

(65) Prior Publication Data
US 2021/0259667 A1 Aug. 26, 2021

Related U.S. Application Data

(60) Provisional application No. 62/980,610, filed on Feb. 24, 2020.

(51) Int. Cl.
*A61B 10/00* (2006.01)
*B01L 3/00* (2006.01)
*A61F 5/455* (2006.01)

(52) U.S. Cl.
CPC ............ *A61B 10/007* (2013.01); *A61F 5/455* (2013.01); *B01L 3/508* (2013.01); *B01L 2300/06* (2013.01); *B01L 2300/0627* (2013.01); *B01L 2300/0809* (2013.01)

(58) Field of Classification Search
CPC ....... A61B 10/007; A61F 5/455; B01L 3/508; B01L 2300/06; B01L 2300/0627; B01L 2300/0809; B01L 2200/026; B01L 2200/028; B01L 2200/087; B01L 2300/047; B01L 2300/0825; B01L 2300/123; B01L 3/502
USPC ........................................................ 600/574
See application file for complete search history.

(56) References Cited

U.S. PATENT DOCUMENTS

| | | |
|---|---|---|
| 3,683,914 A | 8/1972 | Crowley |
| 3,776,235 A | 12/1973 | Ratcliffe et al. |
| 3,941,699 A | 3/1976 | Tyres |
| 4,492,258 A | 1/1985 | Lichtenstein et al. |
| 4,494,581 A | 1/1985 | Gordon |
| 4,563,183 A | 1/1986 | Barrodale et al. |
| 4,799,928 A | 1/1989 | Crowley |

(Continued)

*Primary Examiner* — Benjamin R Whatley
*Assistant Examiner* — Jacqueline Brazin
(74) *Attorney, Agent, or Firm* — Perman & Green, LLP

(57) ABSTRACT

A female urinary diagnostic device including a urine stream collection container having a discharge opening and a stream collection opening, the stream collection opening being configured to surround and isolate a urethral opening, a probe guide passage configured for interior engagement with a vaginal opening for placement of the stream collection opening relative to the urethral opening, and an internal baffle that defines an interior wall of the urine stream collection container that provides a spillway from the stream collection opening to the discharge opening and cooperates with at least a urine sensing device, where the spillway provides urine passage to the urine sensing device and a collection tank, wherein the internal baffle forms at least a portion of the probe guide passage and defines a sounding probe guide surface that positions a sounding probe within the vaginal opening.

18 Claims, 11 Drawing Sheets

(56) References Cited

U.S. PATENT DOCUMENTS

| | | | |
|---|---|---|---|
| 5,257,984 A | | 11/1993 | Kelley |
| 5,457,823 A | | 10/1995 | Mojena |
| 5,511,557 A | | 4/1996 | Hazard et al. |
| 5,586,085 A | * | 12/1996 | Lichte .................... G01F 25/20 367/99 |
| 6,428,521 B1 | | 8/2002 | Droll |
| 9,301,870 B2 | | 4/2016 | Shelton et al. |
| 10,335,121 B2 | | 7/2019 | Desai |
| 10,582,913 B2 | | 3/2020 | Ealovega et al. |
| 10,682,124 B2 | | 6/2020 | Duval |
| 2002/0131902 A1 | | 9/2002 | Levy |
| 2005/0082290 A1 | | 4/2005 | Fask et al. |
| 2007/0025886 A1 | | 2/2007 | Yong |
| 2008/0156092 A1 | * | 7/2008 | Boiarski ............... A61F 5/4404 73/304 R |
| 2008/0251490 A1 | | 10/2008 | Livingston et al. |
| 2011/0094319 A1 | | 4/2011 | Yong |
| 2015/0157300 A1 | | 6/2015 | Ealovega et al. |
| 2018/0103934 A1 | | 4/2018 | Ealovega et al. |
| 2018/0228642 A1 | * | 8/2018 | Davis ................... A61F 5/4408 |

\* cited by examiner

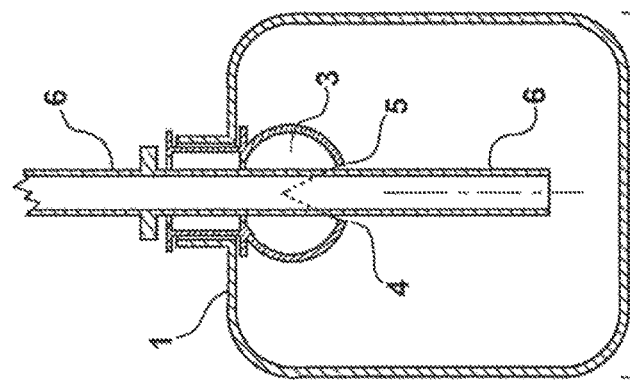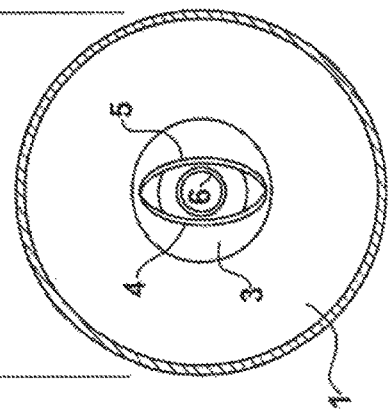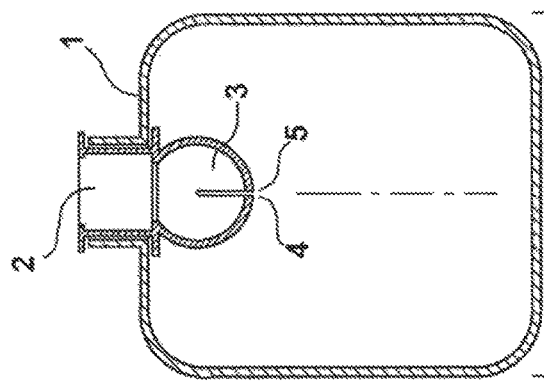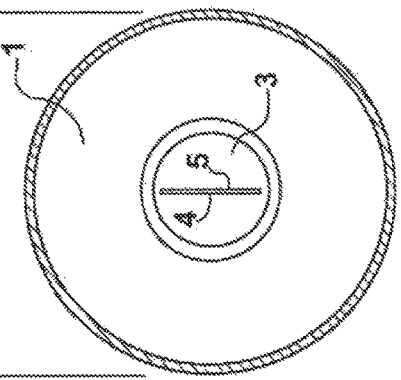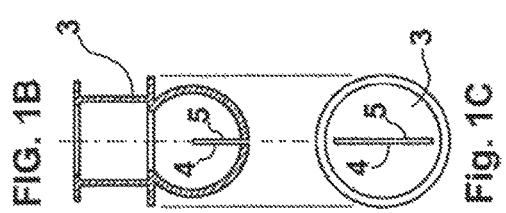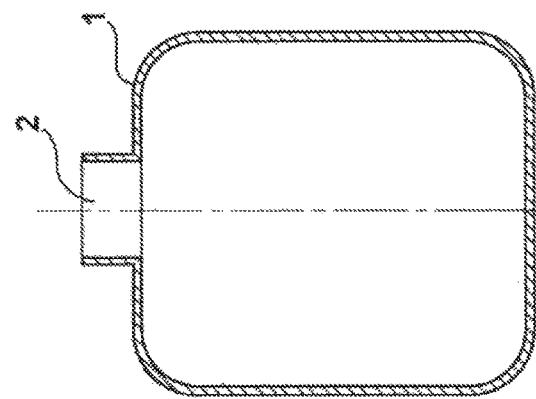

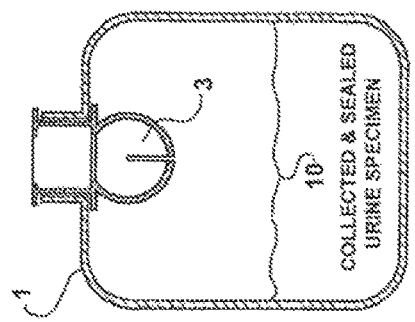
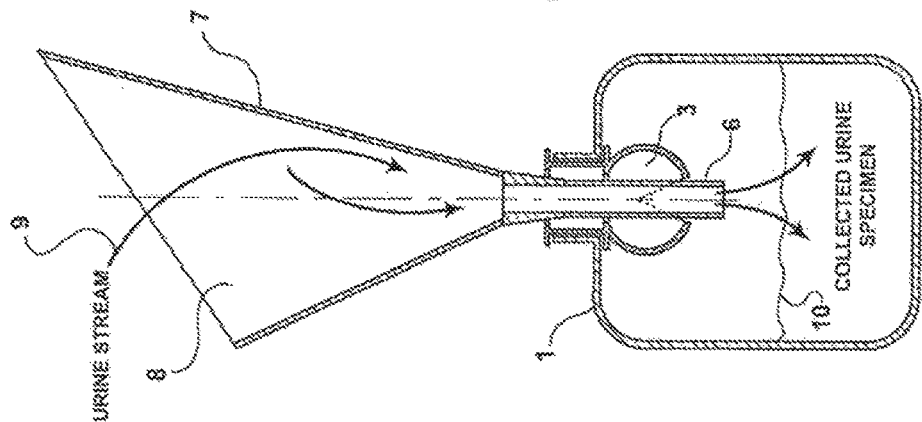
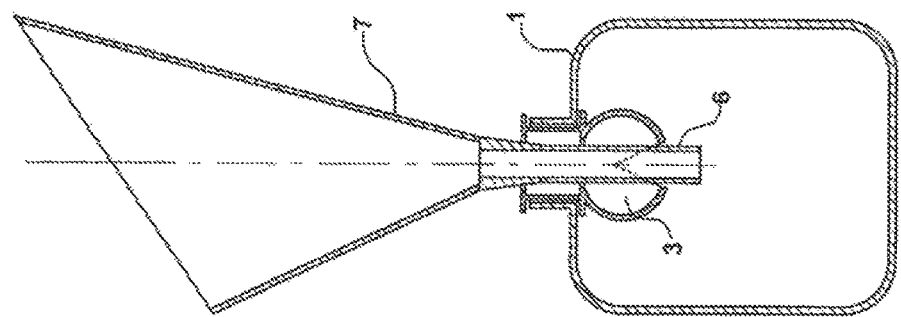
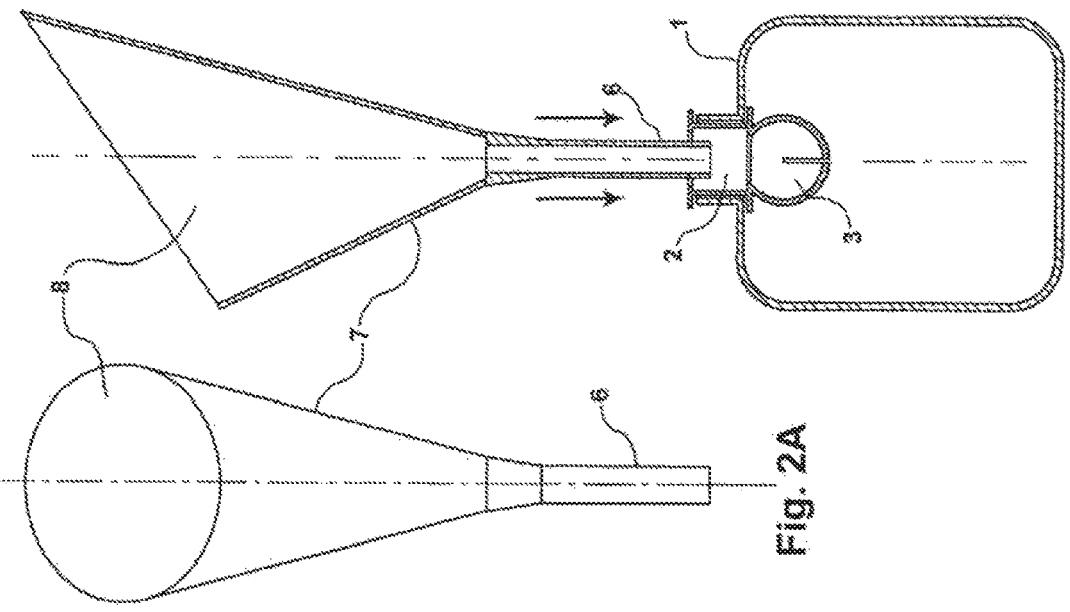

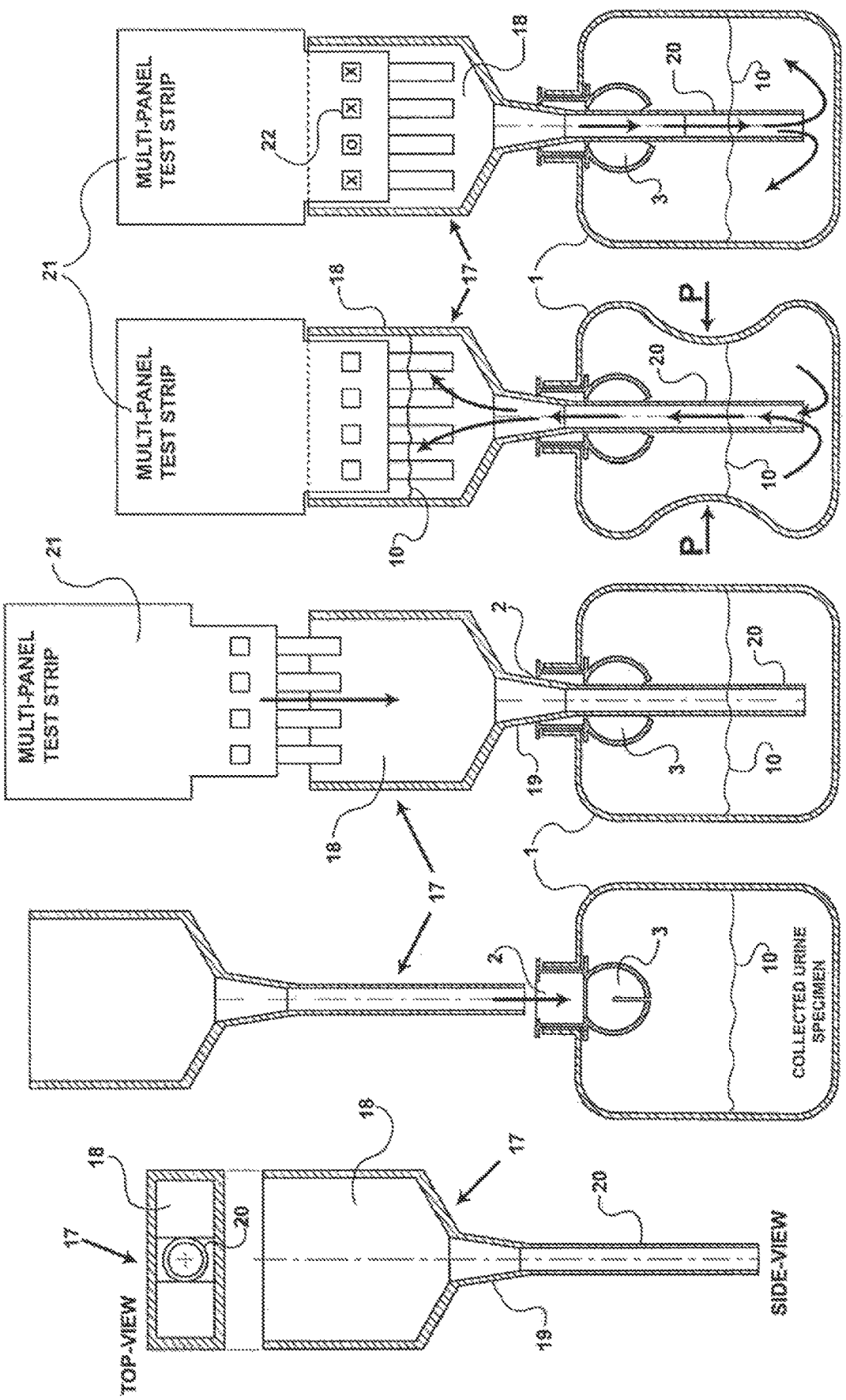

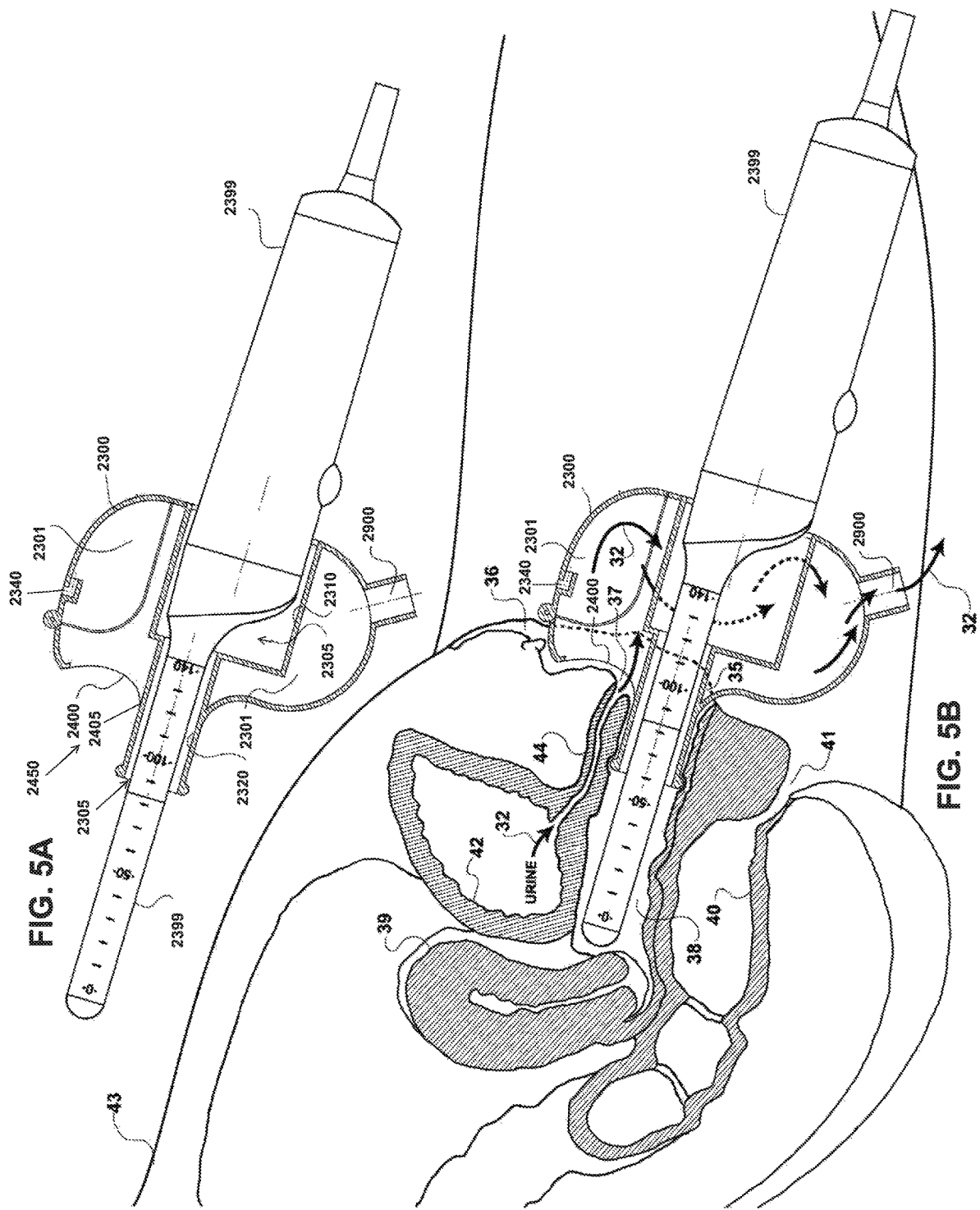

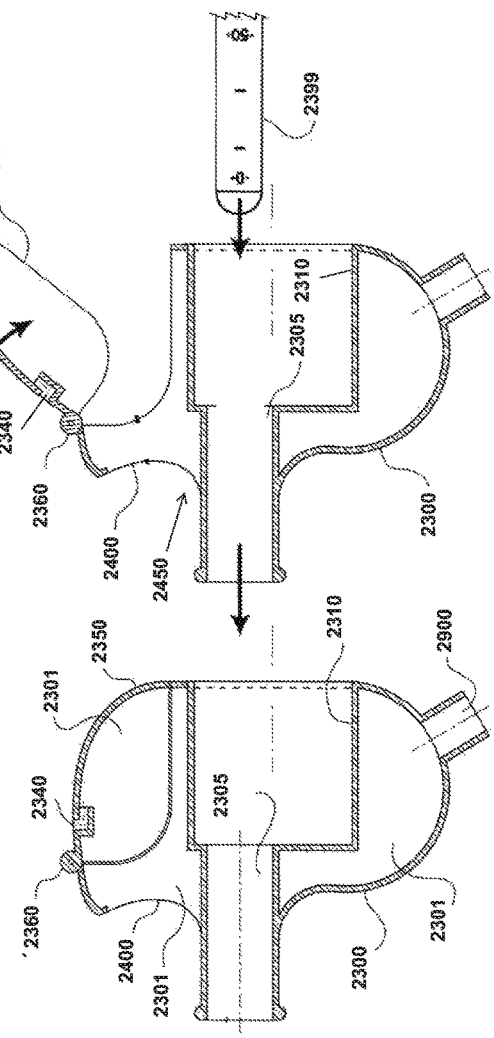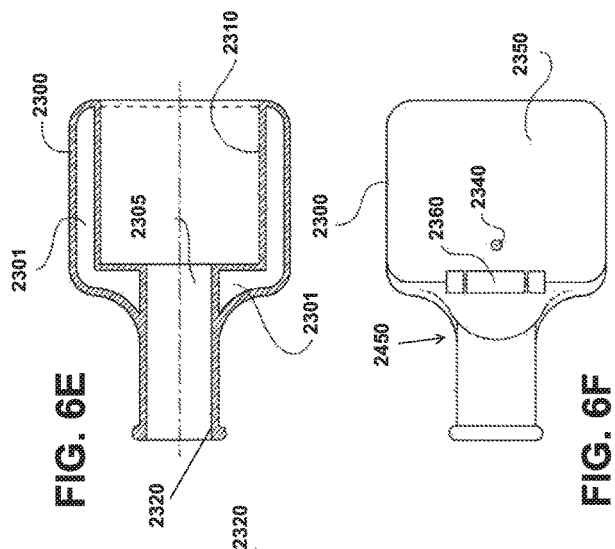

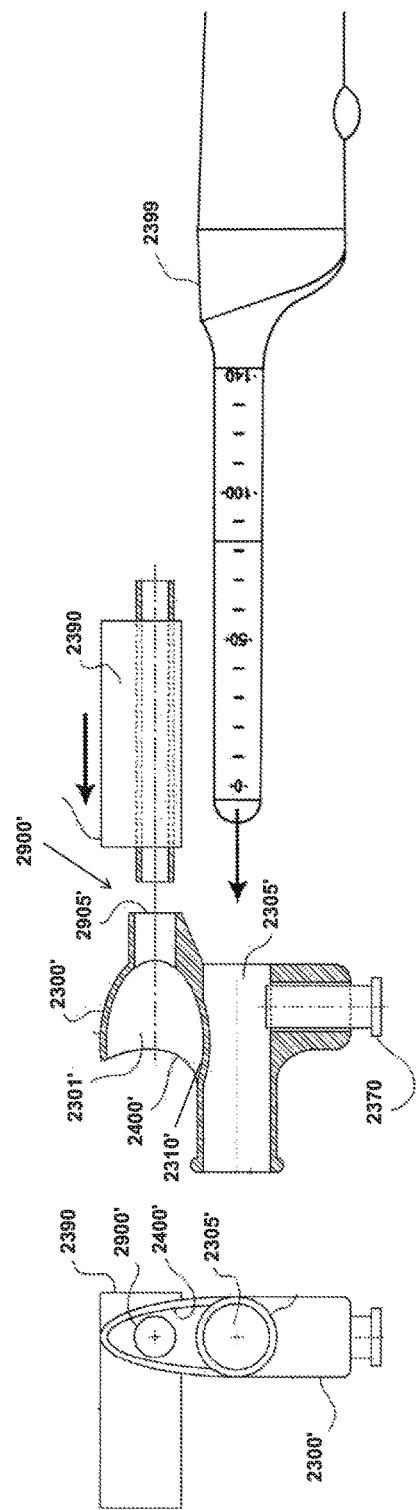
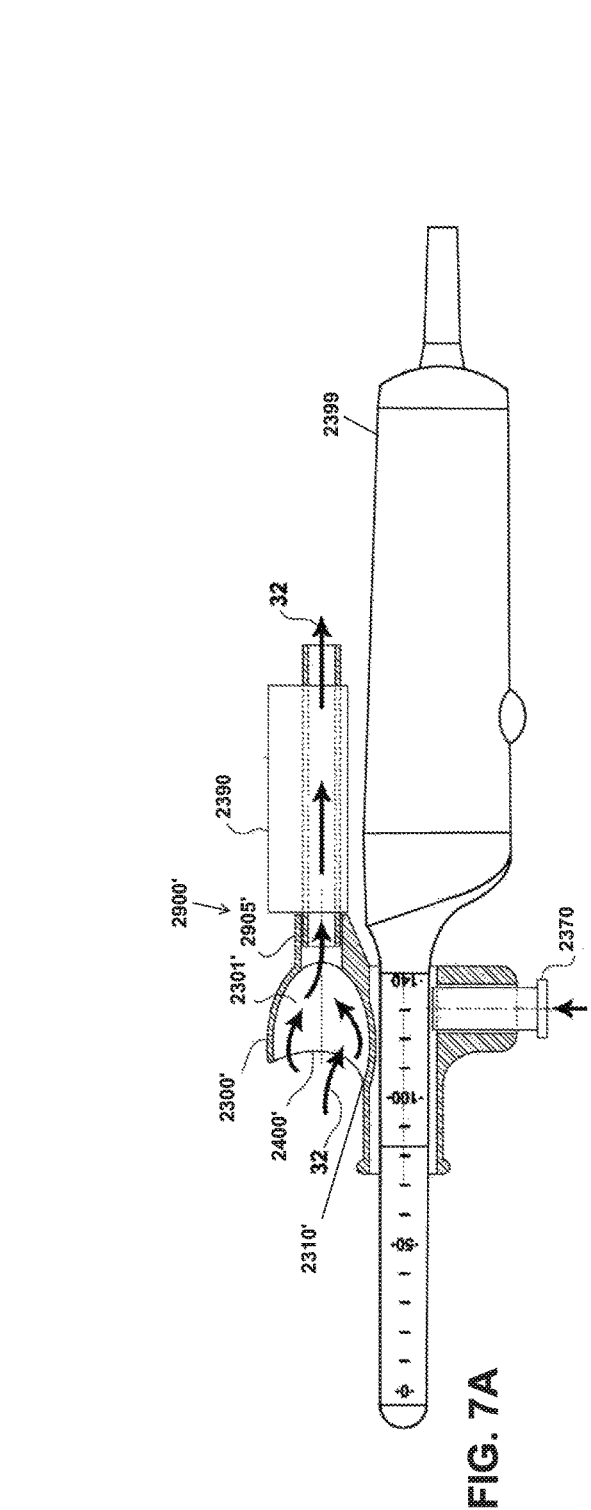

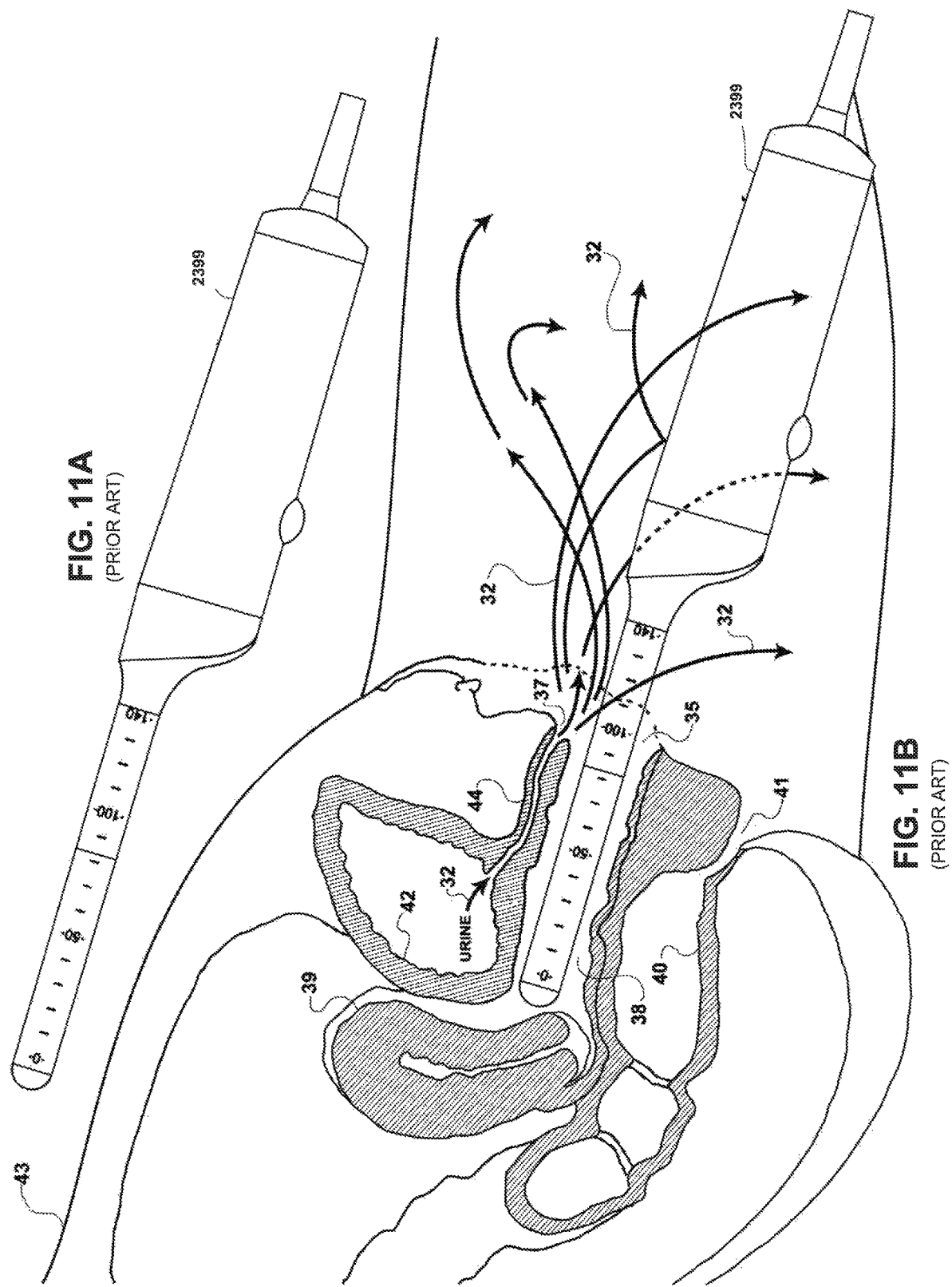

FEMALE URINARY DIAGNOSTIC DEVICE

CROSS-REFERENCE TO RELATED APPLICATIONS

This application is non-Provisional which claims priority from and the benefit of U.S. Provisional Patent Application No. 62/980,610 filed on Feb. 24, 2020, the disclosure of which is incorporated by reference herein in its entirety.

BACKGROUND

1. Field

The disclosed embodiment relates to the collection of a human urine-specimen, the storage of said urine-specimen and the primary testing or analysis of said urine-specimen.

2. Brief Description of Related Developments

A Video Urodynamic Ultrasound test is a diagnostic procedure which involves monitoring a female patient voiding her full bladder while a vaginal ultrasound transducer probe is inserted within her vagina in order to visually monitor and record the contracting bladder from a full condition to an empty condition. It should be obvious that the patient, the doctor and or medical technicians might experience a fair amount of stress, discomfort and embarrassment as the free-flowing urine is expelled all over the ultrasound transducer probe, the doctor's hands holding the ultrasound transducer probe, over the patient herself and the examination table, floor, etc. Embarrassment and discomfort aside, there are some very serious urine contamination and other hygienic issues to consider in addition to the time, effort, and cost involved in cleaning up and decontamination each and every time such a procedure is performed.

Referring to FIGS. 11A-11B, illustrated is a conventional ultrasound transducer probe 2399, e.g., a "BK MEDICAL-MODEL ENDOCAVITY 3DX14LA", but any other suitable vaginal/rectal ultrasound transducer could be utilized. One of the major negative aspects of performing a conventional Video Urodynamic Ultrasound test on a female patient involves collecting video ultrasound data as a bladder contracts from a full condition to an empty condition. Currently, during the conventional Video Urodynamic Ultrasound test, there is no control or restriction on the flow of the urine stream 32 during release of the urine from the bladder. Because of the close proximity of the female urethral opening 37 to the ultrasound transducer probe 2399, the staff performing this procedure must contend with the urine 32 freely flowing over and contaminating the patient, the exam table, the urologist performing the procedure, the ultrasound transducer probe 2399 and possibly anything else in the immediate vicinity. Thus, it would be advantageous to capture, contain, and redirect the urine flow into a suitable container to substantially reduce the negative stress and contamination factors previously mentioned.

A second negative factor related to the conventional Video Urodynamic Ultrasound Test is that because there is no control over the urine stream 32, there are no other diagnostic tests that may be performed simultaneously such as an Uroflowmetry test. Under current medical procedures, getting additional diagnostic urodynamic data such as urine flow rate, urine flow duration, urine flow intervals, urine stream pressure, urine volume, etc. is normally and currently gathered through one or more separate Uroflowmetry test procedures during one or more separate visits to the Urologist's clinic. By combining the two and possibly three of the most commonly performed female urodynamic tests into one procedure, both clinic and urologist time and costs can be significantly reduced. By having the data from each test procedure correlated and synchronized at one central collection point for review, the data gathered becomes significantly more informative and valuable. Additionally, the time saved in both cleanup and decontamination efforts after a Video Urodynamic Ultrasound test also becomes a major time and cost saving consideration.

BRIEF DESCRIPTION OF THE DRAWINGS

The foregoing aspects and other features of the disclosed embodiment are explained in the following description, taken in connection with the accompanying drawings, wherein:

FIG. 1A is a cross-sectional side-view of the urine-specimen-container in accordance with aspects of the disclosed embodiment;

FIG. 1B is a cross-sectional side-view of a check valve of the urine specimen container of FIG. 1A in accordance with aspects of the disclosed embodiment;

FIG. 1C is a bottom exterior view of the check valve of FIG. 1B in accordance with aspects of the disclosed embodiment;

FIG. 1D is a cross-sectional side-view of the urine specimen container and the check valve of FIGS. 1A-1C in accordance with aspects of the disclosed embodiment;

FIG. 1E illustrates the urine specimen container of FIG. 1A co-operating with a tubular object in accordance with aspects of the disclosed embodiment;

FIG. 1F is a cross-sectional bottom view of the urine specimen container of FIG. 1A in accordance with aspects of the disclosed embodiment;

FIG. 1G is a cross-sectional bottom view of the urine specimen container of FIG. 1A in accordance with aspects of the disclosed embodiment;

FIG. 2A illustrates a urine collection attachment in accordance with aspects of the disclosed embodiment;

FIG. 2B is a cross-sectional side view of the urine collection attachment of FIG. 2A in accordance with aspects of the disclosed embodiment;

FIG. 2C illustrates the urine collection attachment of FIG. 2A properly attached to the urine specimen container of FIG. 1A in accordance with aspects of the disclosed embodiment;

FIG. 2D illustrates a urine stream flowing into the urine collection attachment and into the urine specimen container in accordance with aspects of the disclosed embodiment;

FIG. 2E illustrates a portion of a urine collection process in accordance with aspects of the disclosed embodiment;

FIG. 4A illustrates a top and side cross-sectional view of a urine test panel container in accordance with aspects of the disclosed embodiment;

FIG. 4B illustrates the urine test panel container of FIG. 4A positioned just prior to being lowered into an access portion of the urine specimen container of FIG. 1A in accordance with aspects of the disclosed embodiment;

FIGS. 4C-4E illustrate the urine test panel container of FIG. 4A properly interfaced with the urine specimen container of FIG. 1A in accordance with aspects of the disclosed embodiment;

FIGS. 5A-5B illustrate a cross-sectional side-view of a female urinary diagnostic device and a cross-sectional side-view of placement of the female urinary diagnostic device in a human pelvic region in accordance with aspects of the disclosed embodiment;

FIGS. 6A-6G illustrate various views of the female urinary diagnostic device of FIG. 5A in accordance with aspects of the disclosed embodiment;

FIG. 7A illustrate a cross-sectional side-view of a female urinary diagnostic device in accordance with another aspect of the disclosed embodiment;

FIGS. 7B-7C illustrate various views of the female urinary diagnostic device of FIG. 7A in accordance with aspects of the disclosed embodiment;

FIGS. 11A-11B illustrate a cross-sectional side-view of a conventional ultrasound transducer probe and a cross-sectional side-view of placement of the conventional ultrasound transducer probe in a human pelvic region.

DETAILED DESCRIPTION

Figure 3A:
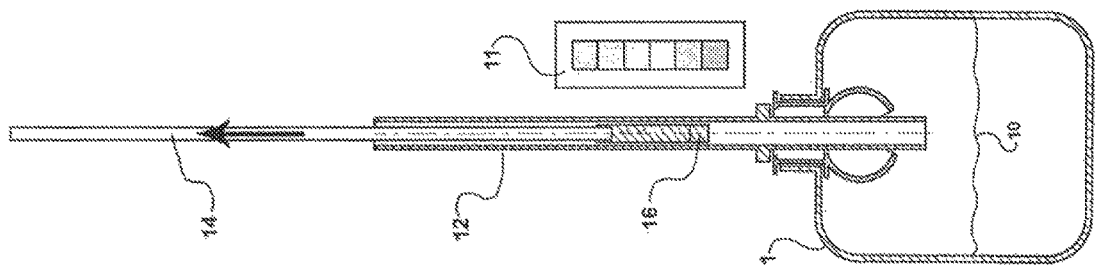
FIG. 3A illustrates components of a urine test strip container assembly in accordance with aspects of the disclosed embodiment.

The instant invention resolves the above noted deficiencies of conventional systems and methods by combining the ultrasound transducer probe and coupling one or more appropriate data collection sensors to a device having similar urine collecting features as the FUD devices described in U.S. patent application Ser. No. 14/557,791 filed on Dec. 2, 2014 and U.S. patent application Ser. No. 15/644,296 filed Jul. 7, 2017, the disclosures of which are incorporated herein by reference in their entireties, to form a new self-contained Uroflowmetry device which is designed to cooperate with the conventional ultrasound transducer probe. This new Uroflowmetry device would have significant advantages over existing Uroflowmetry devices in that it would allow various types of diagnostic data to be collected at or near the actual source of the urine stream, that being the urethral opening itself as opposed to current Uroflowmetry devices which attempt to gather and interpret limited information related to urine flow at some distance from the source. New and significantly more accurate and informative data may now be collected such as but not limited to urine-stream temperature, urine stream force/pressure at the source along with urine flow rate, urine flow duration, urine flow intermittent stoppages and voided urine volume.

Referring to FIGS. 5A-5B, a female urinary diagnostic device 2300 for performing a Video Urodynamic Ultrasound Test is illustrated. The female urinary diagnostic device 2300 is configured to cooperate with the ultrasound transducer probe 2399 (also referred to herein as a sounding probe) so as to provide an efficient and cost effective Video Urodynamic Ultrasound diagnostic tool which substantially reduces urine stream contamination and also provides for substantially simultaneous gathering of data from the urine stream 32 such as the data gathered from a Uroflowmetry test procedure.

Such a diagnostic device offers certain advantages reported herein arising from urine stream collection to specimen containers such as shown in FIGS. 1A-4E and described below. First: the issue of potential contamination of the interior of said urine-specimen-container (also referred to as a urine-storage-container) (1) through physical contact by the patient or the medical staff is removed by the elimination of a need for a traditional screw-on lid through the implementation of an automatically self-closing check-valve device (3) regulating access to the interior of said urine-storage-container. A human hand or finger simply cannot physically pass through said check-valve and come into physical contact with the interior of said urine-specimen-container (1) or its contents.

Second: by virtue of the over-all design of said check-valve (3), accidental spillage of the contents of said urine-specimen-container (1) is also eliminated.

Third: through the implementation of a separate attachable urine-collection (6, 7, 12, 17) device designed to co-operate with said check-valve (3), said urine-specimen-container (1) is kept some distance away from the urine-stream during urine collection thereby significantly reducing the risk of urine coming into contact with either the urine-specimen-container's exterior or with the patient's hand holding the urine-specimen-container (1).

Fourth: through the implementation of a separate attachable urine test-strip-container device (12) designed to co-operate with said check-valve (3), any test-strips or reagents exposed to the urine specimen are at all times safely enclosed and isolated away from human contact within said test-strip container device (17).

Fifth: as the test-strips and reagents are at all times contained within said test-strip container device (17) and because the test-strip container (12) remains attached to the urine-specimen-container (1) until after the test-strip is analyzed, the potential issue of a test-strip being miss-matched to another patient's urine-specimen-container is eliminated.

Sixth: (The aforementioned BD VACUTAINER™ system includes a semi-exposed hypodermic needle attached to the lid of the specimen-cup container. Although there is a prominent warning label referring to this needle, medical staff commonly feels the need to warn patients of the danger of this needle while providing a urine-specimen. The aspects of the disclosed embodiment are designed to be able to co-operate with the BD VACUTAINER™ system is such a way as to limit potential exposure to the needle to trained medical staff only, thus making the system substantially safer for patients.

At no time during the whole process of urine-specimen collection through urine-specimen analysis is the urine-specimen exposed to human contact while properly implementing the aspects of the disclosed embodiment.

According to one aspect of the disclosed embodiment, a urine-specimen-container (1) includes a flat exterior bottom surface and an opposing upper access portal incorporating a check-valve device (3) having a normal closed condition. Said check-valve (3) is designed to co-operate with any number of interchangeable system attachments (6, 7, 12, 17), that in one aspect may be considered a set, each of which can cause said check-valve to have an open condition when properly attached to said urine-specimen-container (1).

In a preferred aspect, said check-valve (3) has a one-piece construction design and is made of a flexible resilient synthetic material, that is, the material has an innate propensity to return to its original manufactured shape after being manually deformed or flexed. In a preferred aspect, said check-valve (3) may have a shape and form not dissimilar to a common infant's feeding bottle nipple; said nipple having a short slit (4) and (5) cleanly cut across the lower end of said nipple allowing for a small tubular object to pass through said slit.

According to another aspect of the disclosed embodiment, said urine-specimen-container (1) may co-operate with a temporarily attached urine-collection device having the sole function of facilitating the collection of urine from a flowing urine-stream. Said urine-collection device (7) may have a funnel shaped reservoir (8) at its top end and a hollow exit-tube (6) at its lower end; said hollow-tube (6) designed to co-operate with said check-valve (3) causing said check-valve (3) to have an open-condition when said hollow-tube (6) is manually passed through said check-valve (3). After a sufficient amount of urine has flowed into said urine-storage-container, said urine-collection device (7) is intended to be detached from said urine-specimen-container (1) and properly disposed of. Detaching said urine-collection device from said urine-storage-container causes said check-valve (3) to automatically resume its original closed condition thereby safely sealing the collected urine specimen within said urine-storage-container.

As the disposable urine-collection device (7) effectively separates the co-operating urine-storage-container by some distance from the urine-stream itself, both the exterior of said urine-storage-container and the patient's hand holding said urine-collection-container are substantially isolated from potential exposure to and contamination by the flowing urine-stream.

According to still another aspect of the disclosed embodiment, said urine-storage-container may co-operate with a temporarily attached urine test-strip-container device (12) having one function of isolating a generic urine test-strip from user contact both before and after said test-strip has been exposed to a urine-specimen and another function of keeping said test-strip physically related to the original urine-specimen-container thereby avoiding potential missmatching of test-strip data to the wrong patient.

Said test-strip-container device (12) may be a simple transparent hollow-tube of sufficient internal diameter to accept a generic urine test-strip within said hollow-tube. Included is a separate slender rod or straw (14) with a means at one end of attaching a generic urine-test-strip; said straw (14) being able to move freely within said hollow-tube and being of a length preferably an inch or two longer then said hollow tube. In a preferred aspect, said straw (14) is indeed a simple common drinking straw of sufficient diameter to allow the non-reagent end of a generic test-strip to be securely lodged a short distance into one end of said straw. Of course, any other efficient means of securing the test-strip to the end of the straw may be employed.

Said test-strip-container device (12) may have an exterior flange (13) located close to its lower end regulating the depth said test-strip-container can be inserted into said urine-storage-container; said test-strip container device (12) is designed to co-operate with said check-valve (3) causing said check-valve (3) to have an open-condition when said test-strip container device (12) is manually passed through said check-valve (3).

With said test-strip-container device (12) properly attached to said urine-specimen-container, said combined rod or straw (14) and test-strip may be pushed downwards into said urine-specimen-container sufficient for the reagent-end of said test-strip to make full contact with the urine-sample collected within said urine-storage-container and immediately withdrawn up into said hollow tube only to a level where said test-strip is still contained within said transparent hollow-tube. After the prescribed waiting period for said generic test-strip, said test-strip may be safely viewed through said transparent hollow-tube and analyzed by comparison to a control-strip according to normal clinic procedure.

After said test-strip-container (12) has served its intended function, said device is intended to be detached from said urine-storage-container and properly disposed of. Detaching said test-strip-container device (12) from said urine-storage-container causes said check-valve to automatically resume its original closed condition thereby safely sealing the original collected urine specimen within said urine-storage-container ready for future testing or proper disposal.

Said test-strip, after making contact with the urine-sample has never been exposed to contact with the medical staff or any work surfaces and the original urine-sample remains at all times securely contained within said urine-storage-container safe from accidental spillage or unwanted contamination.

According to another aspect of the disclosed embodiment, said urine-storage-container may co-operate with an alternative temporarily attached test-strip or reagent container device (17); said alternative design intended to facilitate the testing of generic multi-panel urine test devices. Said alternative design being a hollow-tube designed to co-operate with said check-valve (3) causing said check-valve (3) to have an open condition when said hollow-tube (20) is passed through said check-valve (3). Said hollow tube may incorporate a transparent reservoir (18) at the top end of said hollow-tube (20), said reservoir sufficient in size and shape to contain one of a variety of commonly used generic multi-panel urine test devices. Said multi-panel test device container may also have a tapered exterior section (19) just below said reservoir designed to co-operate with said access portal (2) of said urine-storage-container forming an airtight seal between said tapered section (19) and said urine-specimen-container (1).

With said multi-panel test device container (17) properly attached to said urine-specimen-container (1) and a multi-panel test device (21) in place within said reservoir (18), said urine-specimen-container (1) may be manually squeezed sufficient to cause the urine sample contained within to flow upwards into said multi-panel container reservoir and just sufficient to temporarily make contact with the lower end of said generic multi-panel test device. Once the multi-panel test-device has been properly exposed to the urine sample, manual pressure is removed from the urine-storage-container thereby causing the urine sample to return to the interior of the urine-storage-container, leaving said urine-test-device container reservoir empty of urine.

After the prescribed waiting period, the multi-panel test device may be read through the transparent walls of said reservoir after which the test-device container device itself may be detached from the urine-storage-container, causing said check-valve to resume its normal closed condition. Said test-device and test device container may now be properly disposed of leaving the original urine-sample safely contained within said urine-storage-container for future testing or proper disposal.

Alternatively, the urine-specimen-container (1) may be coupled to a discharge opening 2900 of the female urinary diagnostic device 2300 illustrated in, e.g., FIGS. 5A-5B so as to cooperate there similar to the FUB as described in U.S. patent application Ser. No. 14/557,791 filed on Dec. 2, 2014 and U.S. patent application Ser. No. 15/644,296 filed Jul. 7, 2017, the disclosures of which were previously incorporated herein by reference.

FIGS. 1A-1G illustrate both the urine-specimen-container and the check-valve device.

FIG. 1A is a cross-sectional side-view of the urine-specimen-container (1) showing the access-portal (2) which serves as access to the interior of said container (1). The urine-specimen-container (1) may be constructed of any suitable material commonly used for such urine-specimen-containers in the medical industry and may be of any size or shape having a flat bottom designed to keep the urine-specimen-container (1) in a stable upright position.

In one aspect the urine specimen container or fluid sample collection device includes at least one fluid conduit penetrator (6, 7, 12, 17) as described herein, and a container and penetration fitment (see, e.g., the combination of container (1), check-valve (3) which includes slit (4, 5) with a valved opening penetration into the container, the valved opening penetration being configured to seal the container (1) and includes a valve, such as check-valve (3) configured to accept through the valve the at least one fluid conduit penetrator to effect a transfer of fluid into and out of the container (1). As described herein the at least one fluid conduit penetrator (6, 7, 12, 17) and the container and penetration fitment are configured for urine specimen collection. In one aspect the at least one fluid conduit penetrator (6, 7, 12, 17) is provided as a set of interchangeable fluid conduit penetrators.

FIG. 1B is a cross-sectional side-view of the check-valve (3) which permanently fits within portal (2) of urine-specimen-container (1). Check-valve (3) includes a slit at its lower end comprising two deformable opposing surfaces noted as surface (4) and surface (5). Surface (4) and surface (5) are shown contacting each other thereby indicating check-valve (3) is in its normal closed condition.

FIG. 1C is a bottom exterior view of the check-valve (3) showing a cleanly cut slit located in the bottom of check-valve (3). Said slit comprises two opposing surfaces (4) and (5) which are designed to have a normal condition such that when said opposing surfaces (4) and (5) meet, they form an effective barrier or seal against the movement of liquids through said check-valve (3).

Check-valve (3) may be constructed of any flexible synthetic material which reliably returns to its original shape and form after being manually deformed or flexed. In other words, the check-valve (3) is resiliently closable where the check-valve automatically opens from an insertion of the at least one fluid conduit penetrator (6, 7, 12, 17) through the check-valve (3). In one aspect, as described herein the check-valve (3) includes a resilient membrane having a slit (4) and (5) where the resilient membrane comprises a bulb having a convex surface extending into the container (1) where the slit (4) and (5) is located on the convex surface so as to be resilient to fluid pressure. The proven and preferred check-valve (3) design shown is very similar to a common infant's feeding-bottle nipple both in material and form with the addition of a slit (4) and (5) added to the end of the nipple. Of course, any other check-valve design with a normal closed condition could also function. An alternative functional design might comprise a flexible membrane with a centrally located pin-sized piercing which could be manually forced to expand radially to cause an open condition which automatically returns to a closed condition when said manually applied force is removed.

FIG. 1D illustrates a cross-sectional side-view of both urine-specimen-container (1) and check-valve (3) with check-valve (3) properly positioned within access-portal (2) of said container (1). Opposing surfaces (4) and (5) of check-valve (3) are seen in contact with each other indicating check-valve (3) is in its normal closed-condition. Any fluid contents contained within urine-specimen-container (1) would thereby be sealed within urine specimen container (1) regardless of the physical position or rotational attitude of said container (1).

FIG. 1E illustrates the urine-specimen-container (1) co-operating with a tubular object or fluid conduit penetrator (6) which is sized to accept urine stream collection. As will be described herein, in one aspect the tubular object (6) is interchangeable from a group of different fluid conduit penetrators (6, 7, 12, 17) each of which is configured for penetration of and interfacing with the check-valve (3) and each having different predetermined characteristics that include, as described herein a hollow tube, a circular funnel, a test panel container, a female urinary device and a collection tube interface. Object (6) is a hollow-tube which represents a sub-part common to each of several attachments designed to attach to and co-operate with said urine-specimen-container (1). Said attachments being designed to facilitate both the collection and the testing of a urine specimen sealed within said urine-specimen-container (1). Attachment sub-part (6) being a hollow-tube which, when inserted through check-valve (3), parts the opposing flexible surfaces (4) and (5) of check-valve (3) thereby allowing for the free movement of fluids through hollow-tube sub-part (6). Sub-part (6) may also represent the lower end of a common laboratory pipette which could be used to extract a sample of the urine from within the urine-specimen-container.

FIG. 1F is a cross-sectional bottom view of urine-specimen-container (1) showing the check-valve (3) with opposing surfaces (4) and (5) in contact with each other thereby indicating check-valve (3) is in a closed condition.

FIG. 1G is a cross-sectional bottom-view of urine-specimen-container (1) showing the check-valve (3) in an open condition caused by the insertion of attachment sub-part (6) which has forced opposing flexible surfaces (4) and (5) to separate and no longer have physical contact with each other. When sub-part (6) is removed, opposing surfaces (4) and (5) of check-valve (3) will automatically resume contact with each other thereby reforming the original liquid-tight seal.

FIGS. 2A-2E illustrate the sequential steps of collecting a urine sample into urine-specimen-container (1) through the implementation of a urine-collection device or attachment (7).

FIG. 2A shows the urine-collection device (7) comprising a circular funnel-like form with the top (8) cut at a bias and a hollow exit-tube (6) at the bottom.

FIG. 2B shows a cross-sectional side view of the urine-collection attachment (7) entering urine-specimen-container (1) through access-portal (2) just prior to co-operating with check-valve (3) which is still in its normal closed condition.

FIG. 2C shows urine-collection attachment (7) properly attached to urine-specimen-container (1). The urine-collection attachment's lower exit-tube (6) has passed through check-valve (3) causing said check-valve (3) to assume its temporary open condition.

FIG. 2D shows a urine-stream (9) flowing into urine-collection attachment (7); passing through exit-tube (6) and finally into urine-specimen-container (1).

FIG. 2E shows the final step in the urine collection process wherein the urine-collection attachment (7), having served its urine collection purpose, has been detached from urine-collection-container (1) and has been properly disposed of. Check-valve (3) has automatically returned to its normal closed condition, thereby safely and automatically sealing the urine sample within urine-collection-container (1). The urine-specimen-container (1) is now ready to be handed over to the medical staff for analysis.

Urine-collection attachment (7) may be constructed of any material which will not contaminate the urine sample. There may be multiple alternative external shapes given to the urine-collection attachment (7) to be determined by such possible factors as the patient's gender, physical size, health condition or possibly even whether the patient is standing or reclining while the urine-specimen is being collected; all the while maintaining the primary function of collecting urine from a flowing urine-stream and simultaneously transferring the urine into said urine-specimen-container.

FIGS. 3A-3E illustrate the sequential steps of testing a urine-sample (10) contained with urine-specimen-container (1) utilizing urine-test-strip container assembly (A) designed to co-operate with said urine-specimen-container (1).

FIG. 3A shows the separate components of the urine test-strip-container assembly (A) comprising: a transparent hollow-tube (12); a rod (14) designed to move freely within said hollow-tube (12) and having a method of attaching a generic urine test-strip (15) to one end of said rod (14); rod (14) preferably being an inch or two longer in length than transparent hollow-tube (12). The bold arrow indicates rod (14) with attached test-strip (15) being inserted into the top end of transparent hollow-tube (12). A flange (13) at the lower end of hollow tube (12) regulates the proper depth to which hollow-tube (12) may be inserted into urine specimen-container (1).

Figure 3B:
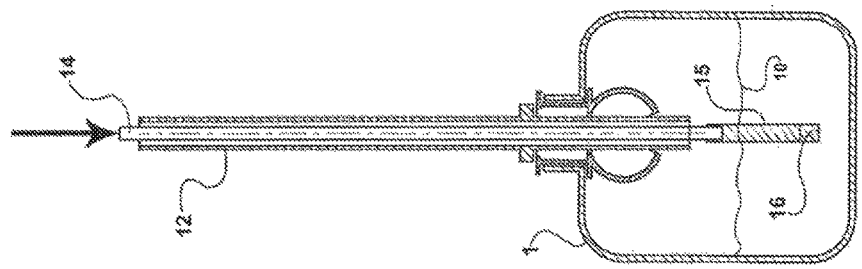
FIG. 3B is a schematic illustration of the urine test strip container assembly of FIG. 3A in accordance with aspects of the disclosed embodiment.

FIG. 3B shows the urine test-strip-container assembly (A) positioned just prior to being inserted into urine-specimen container (7) which has a urine sample (10) ready to be analyzed. Check-valve (3) is seen in FIG. 2 in its normal closed and sealed condition.

Figure 3C:
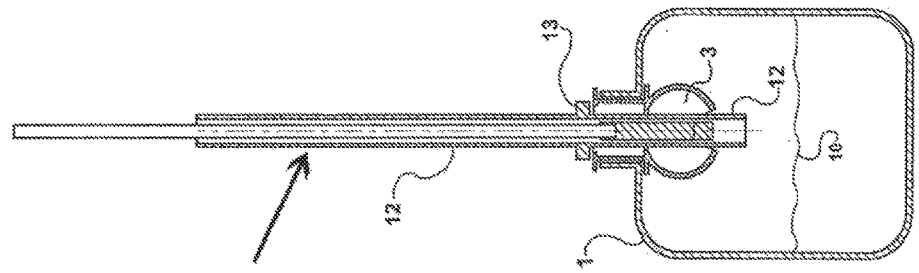
FIGS. 3C-3E illustrate the urine test strip container of FIG. 3A properly attached to the urine specimen container of FIG. 1A in accordance with aspects of the disclosed embodiment.

FIG. 3C shows the assembled urine test-strip-container assembly (A) properly attached to urine-specimen-container (1) and co-operating with check-valve (3) now seen in its temporary open condition.

Figure 3D:
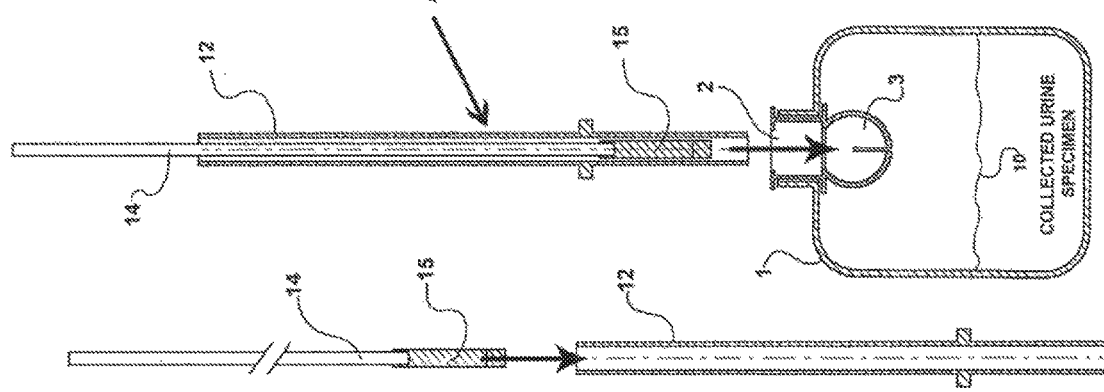

FIG. 3D shows the rod (14) having been manually pushed downwards into transparent hollow-tube (12) causing the reagent-end (16) of test-strip (15) to momentarily dip below the surface of the urine-sample (10).

Figure 3E:
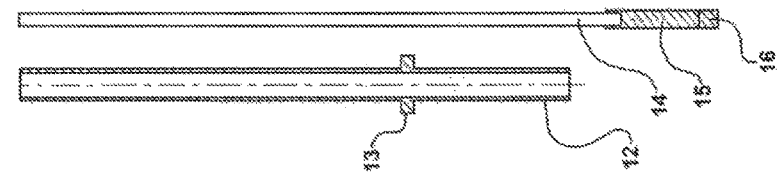

FIG. 3E shows rod (14) and attached test-strip (15) being drawn upwards within transparent hollow-tube (12) to a position similar to that seen in FIG. 5 wherein the test strip is clearly visible but still contained within transparent hollow-tube (12). After the prescribed waiting period for the specific type of test-strip, the color of the reagent-end (16) of the urine-test strip (15) may be visually compared to a control-strip (11) for proper primary analysis of the urine sample.

The final step of the total procedure is the detachment and sanitary disposal of the urine test-strip-container assembly (A) leaving the original urine sample (10) safely and securely sealed within the urine-specimen-container (1) as it is seen back in FIG. C2. Urine-specimen-container (1) may now be stored for future testing or be properly disposed of.

At no time from the point of urine collection to final disposal of all components of the disclosed embodiment has the urine sample been exposed to contact by either the patient or the medical staff involved in the procedure.

FIGS. 4A-4E illustrate the sequential steps of analyzing a urine-sample contained within urine-specimen-container (1) utilizing a urine test-panel-container (17) designed to attach to and co-operate with said urine-specimen-container (1).

FIG. 4A shows top and side cross-sectional views of said urine-test-panel-container (17) Said test-panel-container comprises a transparent upper rectangular reservoir (18) with a lower exit-tube (20) having an upper tapered section (19).

FIG. 4B shows urine test-panel-container (17) positioned just prior to being lowered into access-portal (2) of urine-specimen-container (1) containing a previously collected urine specimen (10). Check-valve (3) is in its normal closed and sealed condition.

FIG. 4C shows test-panel-container (17) properly attached to urine-specimen-container (1) having caused check-valve (3) to assume an open condition. The tapered section (19) of exit-tube (20) is and must be seated firmly within urine-specimen-container entrance-portal (2) forming an air-tight seal. Also shown is a generic four-panel urine-test-panel (21) being lowered into reservoir (18).

FIG. 4D shows urine-specimen-container (1) being manually compressed at points (P-P) thereby forcing the collected urine-specimen (10) to flow upwards into reservoir (18) of test-panel-container (17) sufficient to cover the lower end of urine-test-panel (21).

FIG. 4E shows urine-specimen-container (1) in its normal uncompressed condition after the external pressure has been removed thereby allowing urine in reservoir (18) to drain back down into urine-specimen-container (1). After a designated waiting period, the analyzed results for urine-test-panel (21) may be read through the transparent sides of test-panel-container (17).

The final step of the total procedure being the detachment and sanitary disposal of the urine test-panel-container (17) leaving the original urine sample safely and securely sealed within the urine-specimen-container (1) with check-valve (3) having automatically returned to its normal closed and sealed condition. Urine-specimen-container (1) may now be stored for future testing or properly disposed of.

At no time from the point of urine collection to final disposal of all the used components of the disclosed embodiment have the urine-sample or the activated urine test-panel been exposed to contact by either the patient or the medical staff involved in the procedure.

Referring again to FIGS. 5A-5B, the female urinary diagnostic device 2300 is configured to cooperate with the ultrasound transducer probe 2399 to form a single combined unit and diagnostic tool. The female urinary diagnostic device 2300 includes a urine stream collection container 2301 having the discharge opening 2900 and a stream collection opening 2400, the stream collection opening 2400 being configured to surround and isolate a urethral opening 37. The female urinary diagnostic device 2300 further includes a probe guide passage 2305 and an internal baffle 2310.

The probe guide passage 2305 is configured for interior engagement with a vaginal opening 35 for placement of the stream collection opening 2400 relative to the urethra opening 37. The probe guide passage 2305 is shaped and sized so as to conform to the shape of the ultrasound transducer probe 2399 allowing the ultrasound transducer probe 2399 to easily move in either direction within the probe guide passage 2305. For example, the probe guide passage 2305 defines a sounding probe guide surface 2320 that positions the ultrasound transducer probe 2399 within the vagina opening 35. The sounding probe guide surface 2320 is configured for positioning the stream collection opening 2400 over the urethral opening 37 and as a passageway and guide for the ultrasound transducer probe 2399. At least part of the probe guide passage 2305 and an edge 2401 of the stream collection opening 2400 of the urine stream collection container 2301 form an integrated interface 2450 configured for placement of the stream collection opening 2400 relative to the urethra opening 37 and substantially simultaneous interior engagement of the probe guide passage 2305 with the vaginal opening 35 for placement of the ultrasound transducer probe 2399 in a predetermined position within the vagina.

In one aspect, the internal baffle 2310 forms at least a portion of the probe guide passage 2305 and defines a sounding probe guide surface 2320 that positions the ultrasound transducer probe 2399 within the vaginal opening 35 against a wall in the vagina. The internal baffle 2310 defines an interior wall of the urine stream collection container 2301 that provides a spillway from the stream collection opening 2400 to the discharge opening 2900. The discharge opening 2900 may cooperate with the urine specimen container 1 (FIG. 1A) as previously described, or may be directed to urine collection. In one aspect, the interior wall substantially surrounds at least part of the probe guide passage 2305. For example, the interior wall has an anterior surface forming the spillway, and a posterior surface, opposite the anterior surface that forms the probe guide surface 2320 within the probe guide passage 2305. In one aspect, the interior wall is disposed around the probe guide passage 2305 so that the stream collection opening 2400 and the discharge opening 2900 of the urine stream collection container 2301 are on opposite sides of the probe guide passage 2305 (e.g., the discharge opening 2900 is located below the probe guide passage 2305 and the stream collection opening 2400 is located above the probe guide passage 2305). In one aspect, the spillway cooperates with at least a urine sensing device or sensor 2390, such as a liquid flow sensor "SENSIRION LIQUID FLOW SENSOR-LD20", a "LABORIE-FLOW-STAR" or any other similar device, so that the spillway provides urine passage to the sensor 2390 and/or a collection tank.

FIG. 5B illustrates the female urinary diagnostic device 2300 positioned over the urethral opening 37 and within the vagina 38 while performing a Video Urodynamic Ultrasound test of a contracting bladder 42. The urine stream 32 can be seen entering the stream collection opening 2400 into the urine stream collection container 2301 of the female urinary diagnostic device 2300, flowing over either side of the internal baffle 2310 and exiting out of the discharge opening 2900 and into an attached sensor 2390 (see FIG. 7A) which may measure such data as urine-flow-rate and volume, to specimen container 1, or to waste discharge. The data collected from the sensor 2390 may be synchronized and correlated to the data collected from the ultrasound transducer probe 2399 at a central data collection point for viewing and analysis. The female urinary diagnostic device 2300 thereby can substantially simultaneously perform two of the most common female urodynamic testing procedures during one clinic visit and procedure which currently requires two separate clinic visits while also substantially reducing the major urine contamination issues normally associated with current Video Urodynamic Ultrasound tests.

Referring also to FIGS. 6A-6G, various views of the female urinary diagnostic device 2300 are illustrated. FIG. 6A is a front view of the female urinary diagnostic device 2300 showing the stream collection opening 2400 which is designed to contact the tissue of the vulva immediately surrounding the urethral opening 37 forming a seal which isolates the urine stream 32 from contact with any tissue outside the perimeter of the stream collection opening 2400. Urine enters the female urinary diagnostic device 2300 via the stream collection opening 2400, fills the urine stream collection container 2301 and exits the female urinary diagnostic device 2300 via the discharge opening 2900. FIG. 6B is a cross-sectional view of the female urinary diagnostic device 2300. The probe passageway 2305, which is comprised of the internal baffle 2310 and the probe guide passage 2320, corresponds to the shape of the ultrasound transducer probe 2399 when the ultrasound transducer probe 2399 is cooperating with the female urinary diagnostic device 2300. The probe guide passage 2305 is designed to fit into the vaginal opening 35 to align the stream collection opening 2400 over the urethral opening while simultaneously guiding the ultrasound transducer probe 2399 into the vagina. The probe passageway 2305 traverses the urine stream collection container 2301 of the female urinary diagnostic device 2300 while still allowing the urine stream 32 to freely flow over and around said the internal baffle 2310 to exit the female urinary diagnostic device 2300 via the discharge opening 2900. This ensures an accurate positioning of the sounding probe 2399 via passageway 2305, coincident substantially with accurate placement of the stream collection opening 2400 of the urethral opening 37, and isolation of urine discharge from the urethral opening 37 during testing from the surrounding environment and persons, including the patient.

In one aspect, the female urinary diagnostic device 2300 further includes air vent 2340 and/or optional observation cover or lid 2350. The air vent 2340 serves to prevent an airlock within the urine stream collection container 2301 which might impede the smooth flow of urine exiting the discharge opening 2900 thereby resulting in inaccurate urine flow data. The lid 2350 may be configured to pivot about a hinge 2360 so as to provide visual ingress into the urine stream collection container 2301 via a viewing aperture. In one aspect, the viewing aperture is configured such that placement of the stream collection opening 2400 relative to the urethra opening 37 is observed through the viewing aperture. FIG. 6C is a cross-sectional view of the female urinary diagnostic device 2300 showing the lid 2350 in its open position which allows the urologist an unobstructed view for more accurate positioning of the stream collection opening 2400 over the urethral opening. Also shown is the tip of the ultrasound transducer probe 2399 probe about to be inserted into and through the probe guide passage 2305. The lid 2350 is further configured to seal the urine stream collection container 2301 when closed. As seen in FIG. 6G, the urine stream 32 enters the stream collection opening 2400 flowing into the urine stream collection container 2301 of the female urinary diagnostic device 2300, around the internal baffle 2310 and finally exits via the discharge opening 2900. In one aspect, the exiting urine may be directed to the sensor 2390 or simply to some the collection tank or another suitable container.

Referring now to FIGS. 7A-7C and 8, another aspect of the female urinary diagnostic device 2300' is illustrated. In this aspect, the female urinary diagnostic device 2300' is substantially similar to the female urinary diagnostic device 2300 described above, however, a common wall 2310' joins the probe guide passage 2305 and the urine stream collection container 2304, isolating the probe guide passage 2305 from the urine stream collection container 2301 and providing a spillway from the stream collection opening 2400' to the discharge opening 2900'. In one aspect, the common wall 2310' forms at least part of the probe guide passage 2305' so that the at least part of the probe guide passage 2305' is defined by the urine stream collection container 2301'. In one aspect, the common wall 2310' forms part of the edge of the stream collection opening 2400'. The at least part of the probe guide passage 2305' and an edge of the stream collection opening 2400' of the urine stream collection container 2301' form an integrated interface 2450' configured for placement of the stream collection opening 2400' relative to the urethra opening 37 and substantially simultaneous interior engagement of the probe guide passage 2305' with the vaginal opening 35 for placement of the ultrasound transducer probe 2399 in a predetermined position. Placement of the stream collection opening 2400' relative to the urethra opening 37 and the probe guide passage 2305' in the vaginal opening 35 provides substantially simultaneous isolated passages respectively for passing the urine stream 32 via the spillway to the sensor 2390 in one of the passages, and for positioning the ultrasound transducer probe 2399 in the predetermined position through the probe guide passage 2305'. The isolated passages provided by the integrated interface are disposed so as to substantially simultaneously direct passage of the urine stream 32 past the sensor 2390 via the spillway in the one of the isolated passages and position the ultrasound transducer probe 2399 in the predetermined position through the other passage to sound a predetermined anatomical region coincident with passage of the urine stream 32.

In this aspect, the female urinary diagnostic device 2300' further includes a coupling 2905 connected to the discharge opening 2900' configured for coupling one or more sensors 2390 to the female urinary diagnostic device 2300'. In another aspect, the discharge opening 2900' is configured so as to define a coupling sized and shaped so as to conformally couple an entry port of the sensor 2390 to the female urinary diagnostic device 2300', so that the sensor 2390 is dependent from the diagnostic device, and the female urinary diagnostic device 2300' and sensor 2390 form an assembled unit. Providing the Uroflowmetry device 2390 attached directly to the female urinary diagnostic device 2300' allows gathering urine-flow data closer to the source of the urine stream 32 (i.e., the urethral opening itself) so that a more varied and possibly more accurate data such as true urine-flow rate, bladder pressure, or even urine temperature, for example, rather than the relatively limited data that is gathered from the sensor 2390 several feet away from the source of the urine stream 32. Because the female urinary diagnostic device 2300' creates a stable platform between the female urinary diagnostic device 2300' and the urethral opening, any category of sensor desired could now be positioned within millimeters of the urethral opening 37 allowing for very accurate and consistent data of whatever type to be collected regarding the urine stream 32 at its very source. This ability could possibly provide similar data currently only available during a Cystometric Urodynamic procedure which is an invasive procedure requiring two internal catheters and anesthetics, a separate clinic visit and unfortunately also commonly results in Urinary Tract Infections.

FIG. 7B is a front view of the female urinary diagnostic device 2300' and the attached sensor 2390. FIG. 7C is a side cross section view of the female urinary diagnostic device 2300'. Urine enters the urine stream collection container 2301' via the stream collection opening 2400' and exits via the discharge opening 2900'. In one aspect, the probe guide passage 2305 may include a coupling 2370 (also referred to as a locking mechanism) configured so as to engage the ultrasound transducer probe 2399 disposed in the probe guide passage 2305 and clamp the ultrasound transducer probe 2399 to the female urinary diagnostic device 2300' so that the female urinary diagnostic device 2300' and ultrasound transducer probe 2399 form an assembled unit. For example, a locking mechanism 2370 is activated once the female urinary diagnostic device 2300' is correctly positioned thereby firmly attaching the female urinary diagnostic device 2300' to the ultrasound transducer probe 2399 forming a single unit.

FIG. 7A illustrates the complete assembled diagnostic device 2300' with the sensor 2390 attached to the female urinary diagnostic device 2300' at the discharge opening 2900'. The ultrasound transducer probe 2399 is firmly locked into position within the probe guide passage 2305' of the female urinary diagnostic device 2300' via locking mechanism 2370.

The pathway of the urine-stream 32 as it enters the stream collection opening 2400' of female urinary diagnostic device 2300' and exits via the discharge opening 2900' entering the sensor 2390 within which liquid flow-data is gathered before exiting the sensor 2390 and continuing into a urine collection tank.

Figure 8:
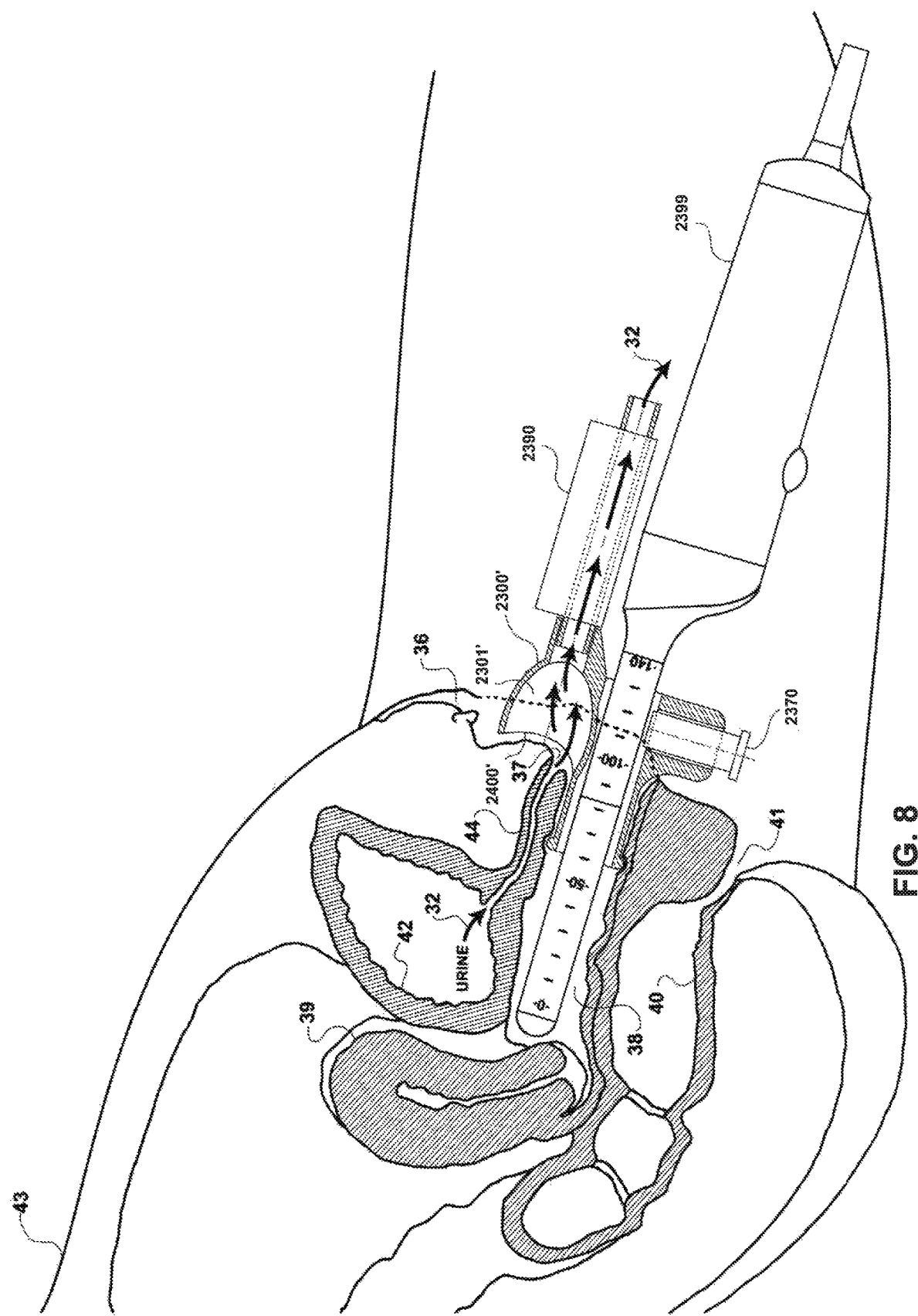
FIG. 8 illustrates a cross-sectional side-view of placement of the female urinary diagnostic device of FIG. 7A in a human pelvic region in accordance with aspects of the disclosed embodiment.

FIG. 8 illustrates the female urinary diagnostic device 2300' as it interfaces with the female anatomy during a combined and simultaneous female Video Urodynamic Ultrasound test and Uroflowmetry test.

Temporarily deactivating the locking Mechanism 2370 allows the ultrasound transducer probe 2399 to move fore and aft while searching for the best video image of the bladder 42. Once the best position is achieved, the locking Mechanism 2370 is re-activated so that gentle forward pressure now ensures a proper seal of the stream collection opening 2400' over the urethral opening 37. Once the act of urination (bladder contraction) begins, data being gathered from both the ultrasound transducer probe 2399 and from the sensor 2390 is being sent to a common data gathering point for future review and analysis.

Figure 9:
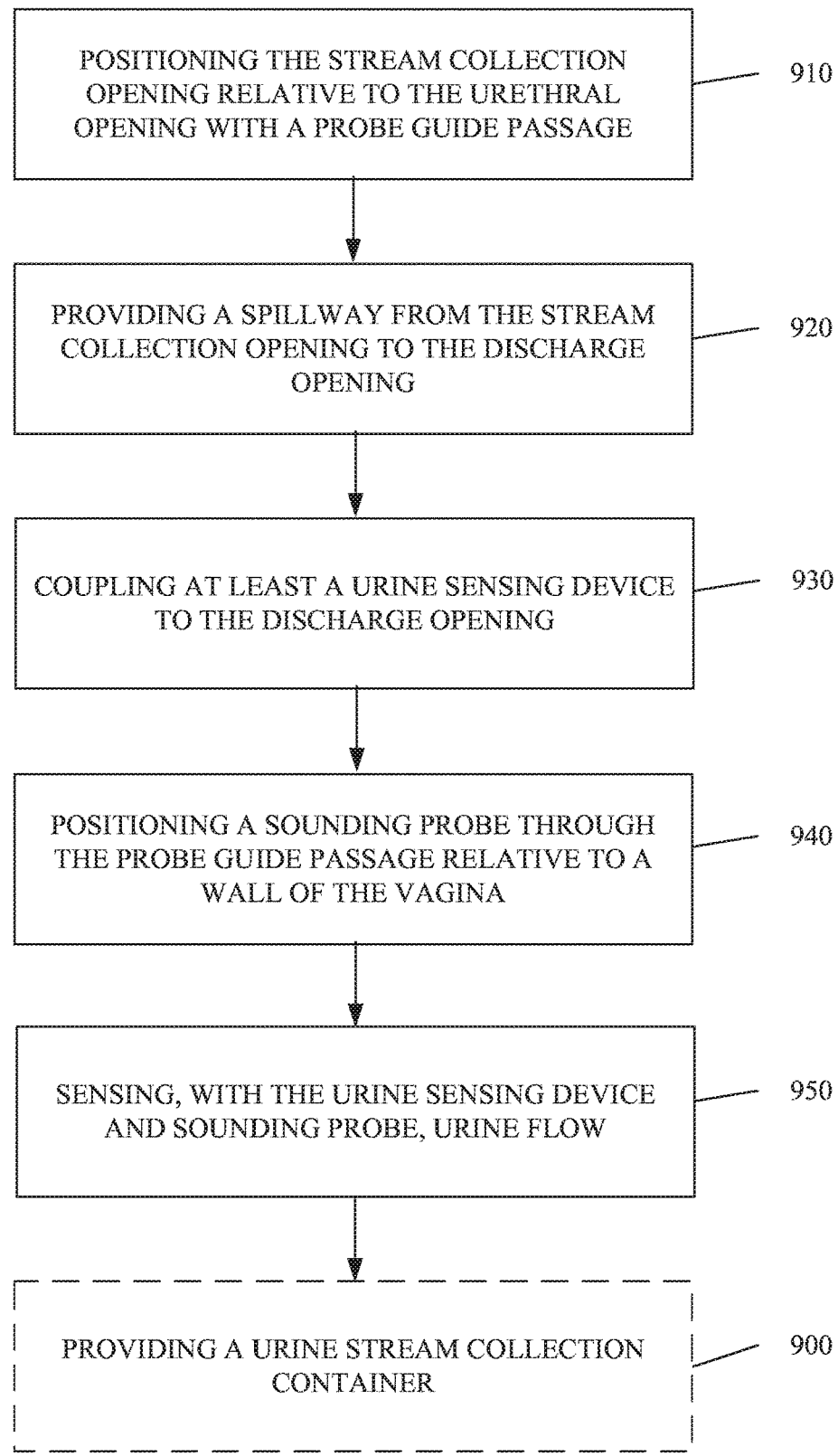
FIGS. 9 and 10 are flow diagrams in accordance with aspects of the disclosed embodiment.
Figure 10:
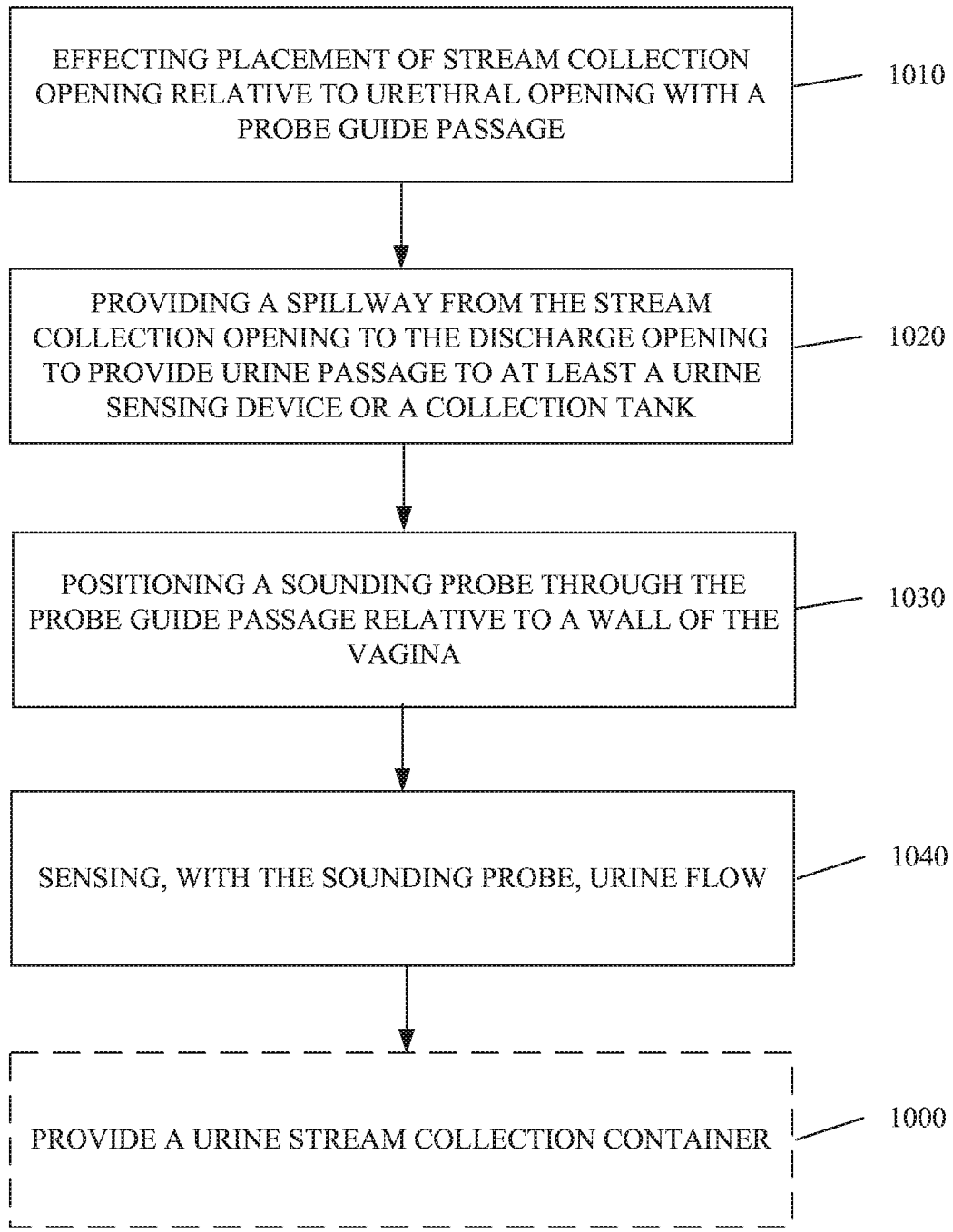

Referring to FIGS. 9 and 10, in one aspect a method of performing a vaginal diagnostic procedure and discharging urine with the female urinary device attachment 2300, 2300' includes providing a urine stream collection container 2301 having a discharge opening 2900 and a stream collection opening 2400 (FIG. 9, Block 900), the stream collection opening 2400 being configured to surround and isolate a urethral opening 37; positioning, with a probe guide passage 2305 configured for interior engagement with a vaginal opening 35, the stream collection opening 2400 relative to the urethral opening 37 (FIG. 9, Block 910); providing a common wall 2310, joining the probe guide passage 2305 and the urine stream collection container 2301 and isolating the probe guide passage 2305 from the urine stream collection container 2301, the common wall providing a spillway from the stream collection opening 2400 to the discharge opening 2900 (FIG. 9, Block 920), wherein the common wall 2310 forms at least part of the probe guide passage 2305 and cooperates with at least a urine sensing device 2390 coupled to the urine stream collection container 2301 (FIG. 9, Block 930); positioning, a sounding probe 2399, through the probe guide passage 2305, in a predetermined position relative to a wall of the vagina (FIG. 9, Block 940); and sensing, with the urine sensing device 2390 or sounding probe 2399, urine flow from the discharge opening 2900 (FIG. 9, Block 950). In one aspect the method includes providing a urine stream collection container 2301 having a discharge opening 2900 and a stream collection opening 2400 (FIG. 10, Block 1000), the stream collection opening 2400 being configured to surround and isolate a urethral opening 37; effecting placement of the stream collection opening 2400 relative to the urethral opening 37 with a probe guide passage 2305 configured for interior engagement with a vaginal opening 35 (FIG. 10, Block 1010); providing an internal baffle that defines an interior wall of the urine stream collection container, the internal baffle forming at least a portion of the probe guide passage, the internal baffle providing a spillway from the stream collection opening to the discharge opening, the spillway cooperating with at least a urine sensing device to provide urine passage to the urine sensing device and a collection tank (FIG. 10, Block 1020); positioning a sounding probe 2399 within the vaginal opening 35 via a sounding probe guide surface defined by the internal baffle 2310 forming at least a portion of the probe guide passage 2305 (FIG. 10, Block 1030) and sensing, with the sounding probe 2399, urine flow from the discharge opening 2900 (FIG. 10, Block 1040).

Because the aspects of the present embodiment allow for urine stream pressure/force, flow rate and volume to be measured at the urethral opening itself, another Urodynamic test known as a Cystometric test which is physically invasive in that it requires the insertion of two catheters and the use of anesthetics could possibly be avoided in many cases. As a Cystometric test measures internal bladder pressure over time and therefore also records changes in bladder pressure caused by involuntary spasms etc., similar data could be also recorded and interpreted by measuring changes in urine stream pressure/force as the urine exits the urethral opening. If the urine flow is temporarily blocked at a point just past the sensor 2390, then the pressure within the bladder and the pressure within the urine stream collection container 2301, 2301' will equalize, in other words, pressure data gathered from within the female urinary diagnostic device 2300, 2300' and sensor 2390 would be the same as pressure data gathered from within the bladder itself thus avoiding the need for an invasive internal Cystometric test as currently performed. An advantage of collecting pressure data at the urethral opening as opposed to within the bladder itself via an internal catheter is that the catheter technically replaces the urethra and therefore should there be any negative conditions or anomalies related to the urethra itself, then these conditions will not be accounted for in the results of the diagnosis. If the Urologist finds the data gathered from a urine pressure/force sensor located at the urethral opening sufficiently informative to avoid an invasive Cystometric test, then the female urinary diagnostic device 2300 would provide data currently requiring three separate procedures performed on three separate clinic visits into data gathered during one single non-invasive procedure requiring only one clinic visit.

Measuring urine stream temperature accurately at the source could prove significant as a temperature above normal could indicate a condition such as a bladder or kidney infection and therefore have a direct correlation or impact on the results relating to the other data that was simultaneously collected.

Additionally, negative pressure could be introduced within the collection tank which would be located past the sensor 2390 (in a closed air-tight system) and the resulting suction would help draw the stream collection opening 2400 more tightly against the vulva forming an even more secure seal against urine leakage than physical hand pressure alone. Also, in order to further inhibit any urine leakage at the stream collection opening 2400, the urine stream collection container 2301 could be divided into two chambers separated by a one-way valve designed to allow urine to flow towards the sensor 2390 but not back out the stream collection opening 2400. Such a valve could be of a common Duckbill design. The second chamber in this embodiment could be flexible or expandable in nature (balloon-like) which would also decrease the likelihood of urine back-flow resulting in possible urine leakage at the stream collection opening 2400.

Reviewing the test results on, e.g., a computer monitor, the urologist will not only see the ultrasound video but will also see displayed one or more other graphs or other forms of data that were simultaneously gathered during the same bladder voiding event. So now, if the video is paused at a specific point where the urologist viewed, for example, an involuntary bladder spasm or any other notable anomaly, the urologist could now accurately confirm this occurrence by viewing the Uroflowmetry graph which would confirm that at that very point in time, an increase in urine stream pressure/force did indeed occur and by how much. By employing the aspects of the disclosed embodiment, the urologist now has significantly more accurate, more informative and more varied data with which to form a significantly more informed diagnosis regarding the patient than previously possible.

In accordance with one or more aspects of the disclosed embodiment a female urinary diagnostic device is provided. The female urinary diagnostic device including a urine stream collection container having a discharge opening and a stream collection opening, the stream collection opening being configured to surround and isolate a urethral opening, a probe guide passage configured for interior engagement with a vaginal opening for placement of the stream collection opening relative to the urethral opening, and an internal baffle that defines an interior wall of the urine stream collection container that provides a spillway from the stream collection opening to the discharge opening and cooperates with at least a urine sensing device, where the spillway provides urine passage to the urine sensing device and a collection tank, wherein the internal baffle forms at least a portion of the probe guide passage and defines a sounding probe guide surface that positions a sounding probe within the vaginal opening.

In accordance with one or more aspects of the disclosed embodiment the sounding probe guide surface positions the sounding probe against a wall of the vaginal opening.

In accordance with one or more aspects of the disclosed embodiment the interior wall has an anterior surface forming the spillway, and a posterior surface, opposite the anterior surface that forms the sounding probe guide surface within the probe guide passage.

In accordance with one or more aspects of the disclosed embodiment the interior wall substantially surrounds at least part of the probe guide passage.

In accordance with one or more aspects of the disclosed embodiment the interior wall is disposed around the probe guide passage so that the stream collection opening and the discharge opening of the urine stream collection container are on opposite sides of the probe guide passage.

In accordance with one or more aspects of the disclosed embodiment the discharge opening is located below the probe guide passage.

In accordance with one or more aspects of the disclosed embodiment the urine stream collection container has a viewing aperture through which placement of the stream collection opening relative to the urethral opening is observed.

In accordance with one or more aspects of the disclosed embodiment at least part of the probe guide passage and an edge of the stream collection opening of the urine stream collection container form an integrated interface configured for placement of the stream collection opening relative to the urethral opening and substantially simultaneous interior engagement of the probe guide passage with the vaginal opening for placement of the sounding probe in a predetermined position.

In accordance with one or more aspects of the disclosed embodiment a method of performing a vaginal diagnostic procedure and discharging urine with a female urinary diagnostic device is provided. The method including providing a urine stream collection container having a discharge opening and a stream collection opening, the stream collection opening being configured to surround and isolate a urethral opening, effecting placement of the stream collection opening relative to the urethral opening with a probe guide passage configured for interior engagement with a vaginal opening, providing an internal baffle that defines an interior wall of the urine stream collection container, the internal baffle forming at least a portion of the probe guide passage, the internal baffle providing a spillway from the stream collection opening to the discharge opening, the spillway cooperating with at least a urine sensing device to provide urine passage to the urine sensing device and a collection tank, and positioning a sounding probe within the vaginal opening via a sounding probe guide surface defined by the internal baffle forming at least a portion of the probe guide passage.

In accordance with one or more aspects of the disclosed embodiment the method further including positioning, with the sounding probe guide surface, the sounding probe against a wall of the vaginal opening.

In accordance with one or more aspects of the disclosed embodiment the interior wall has an anterior surface forming the spillway, and a posterior surface, opposite the anterior surface that forms the sounding probe guide surface within the probe guide passage.

In accordance with one or more aspects of the disclosed embodiment the interior wall substantially surrounds at least part of the probe guide passage.

In accordance with one or more aspects of the disclosed embodiment the interior wall is disposed around the probe guide passage so that the stream collection opening and the discharge opening of the urine stream collection container are on opposite sides of the probe guide passage.

In accordance with one or more aspects of the disclosed embodiment the discharge opening is located below the probe guide passage.

In accordance with one or more aspects of the disclosed embodiment the urine stream collection container has a viewing aperture through which placement of the stream collection opening relative to the urethral opening is observed.

In accordance with one or more aspects of the disclosed embodiment at least part of the probe guide passage and an edge of the stream collection opening of the urine stream collection container form an integrated interface, the method further comprising positioning, with the integrated interface, the stream collection opening relative to the urethral opening and substantially simultaneous engaging an interior of the vaginal opening with the probe guide passage for placement of the sounding probe in a predetermined position.

In accordance with one or more aspects of the disclosed embodiment a female urinary diagnostic device is provided. The female urinary diagnostic device including a urine stream collection container having a discharge opening and a stream collection opening, the stream collection opening being configured to surround and isolate a urethral opening, a probe guide passage configured for interior engagement with a vaginal opening for placement of the stream collection opening relative to the urethral opening, and a common wall, joining the probe guide passage and the urine stream collection container and isolating the probe guide passage from the urine stream collection container, wherein the common wall provides a spillway from the stream collection opening to the discharge opening and cooperates with at least a urine sensing device coupled to the urine stream collection container to sense flow from the discharge opening, wherein the common wall forms at least part of the probe guide passage, and wherein the probe guide passage is configured so as to receive a sounding probe through the probe guide passage and position the sounding probe in a predetermined position relative to a wall of the vagina.

In accordance with one or more aspects of the disclosed embodiment the common wall forms at least part of the probe guide passage so that the at least part of the probe guide passage is defined by the urine stream collection container.

In accordance with one or more aspects of the disclosed embodiment at least part of the probe guide passage and an edge of the stream collection opening of the urine stream collection container form an integrated interface configured for placement of the stream collection opening relative to the urethral opening and substantially simultaneous interior engagement of the probe guide passage with the vaginal opening for placement of the sounding probe in the predetermined position.

In accordance with one or more aspects of the disclosed embodiment the common wall forms part of the edge of the stream collection opening.

In accordance with one or more aspects of the disclosed embodiment at least part of the probe guide passage and an edge of the stream collection opening of the urine stream collection container form an integrated interface configured for placement of the stream collection opening relative to the urethral opening and interior engagement of the probe guide passage with the vaginal opening to provide substantially simultaneous isolated passages respectively for passing a urine stream via the spillway to the urine sensing device in one of the isolated passages, and for positioning the sounding probe in the predetermined position through another of the isolated passages.

In accordance with one or more aspects of the disclosed embodiment the isolated passages provided by the integrated interface are disposed so as to substantially simultaneously direct passage of urine stream past the urine sensing device via the spillway in the one of the isolated passages and position the sounding probe in the predetermined position through the other isolated passage to sound a predetermined anatomical region coincident with passage of the urine stream.

In accordance with one or more aspects of the disclosed embodiment the female urinary diagnostic device further including a coupling connected to the discharge opening configured for coupling the urine sensing device to the discharge opening.

In accordance with one or more aspects of the disclosed embodiment the discharge opening is configured so as to define a coupling sized and shaped so as to conformally couple an entry port of the urine sensing device to the female urinary diagnostic device, so that the urine sensing device is dependent from the female urinary diagnostic device, and the female urinary diagnostic device and urine sensing device form an assembled unit.

In accordance with one or more aspects of the disclosed embodiment the probe guide passage comprises a coupling configured so as to engage the sounding probe disposed in the probe guide passage and clamp the sounding probe to the diagnostic device so that the diagnostic device and sounding probe form an assembled unit.

In accordance with one or more aspects of the disclosed embodiment a method of performing a vaginal diagnostic procedure and discharging urine with a female urinary diagnostic device is provided. The method including providing a urine stream collection container having a discharge opening and a stream collection opening, the stream collection opening being configured to surround and isolate a urethral opening, positioning, with a probe guide passage configured for interior engagement with a vaginal opening, the stream collection opening relative to the urethral opening, providing a common wall, joining the probe guide passage and the urine stream collection container and isolating the probe guide passage from the urine stream collection container, the common wall providing a spillway from the stream collection opening to the discharge opening, wherein the common wall forms at least part of the probe guide passage and cooperates with at least a urine sensing device coupled to the urine stream collection container, positioning, a sounding probe, through the probe guide passage, in a predetermined position relative to a wall of the vagina and sensing, with the urine sensing device or sounding probe, urine flow.

In accordance with one or more aspects of the disclosed embodiment the common wall forms at least part of the probe guide passage so that the at least part of the probe guide passage is defined by the urine stream collection container.

In accordance with one or more aspects of the disclosed embodiment at least part of the probe guide passage and an edge of the stream collection opening of the urine stream collection container form an integrated interface, the method further comprising positioning, with the integrated interface, the stream collection opening relative to the urethral opening and substantially simultaneous engaging an interior of the vaginal opening with the probe guide passage for placement of the sounding probe in the predetermined position.

In accordance with one or more aspects of the disclosed embodiment the common wall forms part of the edge of the stream collection opening.

In accordance with one or more aspects of the disclosed embodiment at least part of the probe guide passage and an edge of the stream collection opening of the urine stream collection container form an integrated interface, the method further comprising positioning, with the integrated interface, the stream collection opening relative to the urethral opening and engaging an interior of the vaginal opening with the probe guide passage to provide substantially simultaneous isolated passages respectively for passing a urine stream via the spillway to the urine sensing device in one of the isolated passages, and for positioning the sounding probe in the predetermined position through another of the isolated passages.

In accordance with one or more aspects of the disclosed embodiment the method further including substantially simultaneously directing passage of urine stream past the urine sensing device via the spillway in the one of the isolated passages and positioning the sounding probe in the predetermined position through the other isolated passage to sound a predetermined anatomical region coincident with passage of the urine stream.

In accordance with one or more aspects of the disclosed embodiment the method further including a coupling connected to the discharge opening configured for coupling the urine sensing device to the discharge opening.

In accordance with one or more aspects of the disclosed embodiment the discharge opening is configured so as to define a coupling sized and shaped so as to conformally couple an entry port of the urine sensing device to the female urinary diagnostic device, so that the urine sensing device is dependent from the female urinary diagnostic device, and the female urinary diagnostic device and urine sensing device form an assembled unit.

In accordance with one or more aspects of the disclosed embodiment the method further including engaging the sounding probe with a coupling disposed in the probe guide passage and clamping the sounding probe to the diagnostic device so that the diagnostic device and sounding probe form an assembled unit.

It should be understood that the foregoing description is only illustrative of the aspects of the disclosed embodiment. Various alternatives and modifications can be devised by those skilled in the art without departing from the aspects of the disclosed embodiment. Accordingly, the aspects of the disclosed embodiment are intended to embrace all such alternatives, modifications and variances that fall within the scope of the appended claims. Further, the mere fact that different features are recited in mutually different dependent or independent claims does not indicate that a combination of these features cannot be advantageously used, such a combination remaining within the scope of the aspects of the disclosed embodiment.

What is claimed is:

1. A female urinary diagnostic device comprising:
    a urine stream collection container having a discharge opening and a stream collection opening, the stream collection opening being sized and shaped so as to contact the tissue of the vulva substantially proximate the urethral opening forming a seal to surround and isolate a urethral opening;
    a probe guide passage sized and shaped for interior engagement with a vaginal opening so as to be securely seated against a wall in the vagina for placement of the stream collection opening relative to the urethral opening; and
    a common wall, joining the probe guide passage and the urine stream collection container and isolating the probe guide passage from the urine stream collection container, wherein the common wall provides a spillway from the stream collection opening to the discharge opening and cooperates with at least a urine sensing device coupled to the urine stream collection container to sense flow from the discharge opening;
    wherein the common wall forms at least part of the probe guide passage, and wherein the probe guide passage is sized and shaped so as to receive a sounding probe through the probe guide passage and position the sounding probe in a predetermined position relative to a wall of the vagina.

2. The female urinary diagnostic device of claim 1, wherein the common wall forms at least part of the probe guide passage so that the at least part of the probe guide passage is defined by the urine stream collection container.

3. The female urinary diagnostic device of claim 1, wherein at least part of the probe guide passage and an edge of the stream collection opening of the urine stream collection container form an integrated interface configured for placement of the stream collection opening relative to the urethral opening and substantially simultaneous interior engagement of the probe guide passage with the vaginal opening for placement of the sounding probe in the predetermined position.

4. The female urinary diagnostic device of claim 3, wherein the common wall forms part of the edge of the stream collection opening.

5. The female urinary diagnostic device of claim 1, wherein at least part of the probe guide passage and an edge of the stream collection opening of the urine stream collection container form an integrated interface configured for placement of the stream collection opening relative to the urethral opening and interior engagement of the probe guide passage with the vaginal opening to provide substantially simultaneous isolated passages respectively for passing a urine stream via the spillway to the urine sensing device in one of the isolated passages, and for positioning the sounding probe in the predetermined position through another of the isolated passages.

6. The female urinary diagnostic device of claim 5, wherein the isolated passages provided by the integrated interface are disposed so as to substantially simultaneously direct passage of urine stream past the urine sensing device via the spillway in the one of the isolated passages and position the sounding probe in the predetermined position through the other isolated passage to sound a predetermined anatomical region coincident with passage of the urine stream.

7. The female urinary diagnostic device of claim 1, further comprising a coupling connected to the discharge opening configured for coupling the urine sensing device to the discharge opening.

8. The female urinary diagnostic device of claim 1, wherein the discharge opening is configured so as to define a coupling sized and shaped so as to conformally couple an entry port of the urine sensing device to the female urinary diagnostic device, so that the urine sensing device is dependent from the female urinary diagnostic device, and the female urinary diagnostic device and urine sensing device form an assembled unit.

9. The female urinary diagnostic device of claim 1, wherein the probe guide passage comprises a coupling configured so as to engage the sounding probe disposed in the probe guide passage and clamp the sounding probe to the diagnostic device so that the diagnostic device and sounding probe form an assembled unit.

10. A method of performing a vaginal diagnostic procedure and discharging urine with a female urinary diagnostic device comprising:
providing a urine stream collection container having a discharge opening and a stream collection opening, the stream collection opening being sized and shaped so as to contact the tissue of the vulva substantially proximate the urethral opening forming a seal to surround and isolate a urethral opening;
positioning, with a probe guide passage sized and shaped for interior engagement with a vaginal opening so as to be securely seated against a wall in the vagina, the stream collection opening relative to the urethral opening;
providing a common wall, joining the probe guide passage and the urine stream collection container and isolating the probe guide passage from the urine stream collection container, the common wall providing a spillway from the stream collection opening to the discharge opening, wherein the common wall forms at least part of the probe guide passage and cooperates with at least a urine sensing device coupled to the urine stream collection container;
positioning, a sounding probe, through the probe guide passage, in a predetermined position relative to a wall of the vagina; and
sensing, with the urine sensing device or sounding probe, urine flow.

11. The method of claim 10, wherein the common wall forms at least part of the probe guide passage so that the at least part of the probe guide passage is defined by the urine stream collection container.

12. The method of claim 10, wherein at least part of the probe guide passage and an edge of the stream collection opening of the urine stream collection container form an integrated interface, the method further comprising positioning, with the integrated interface, the stream collection opening relative to the urethral opening and substantially simultaneous engaging an interior of the vaginal opening with the probe guide passage for placement of the sounding probe in the predetermined position.

13. The method of claim 12, wherein the common wall forms part of the edge of the stream collection opening.

14. The method of claim 10, wherein at least part of the probe guide passage and an edge of the stream collection opening of the urine stream collection container form an integrated interface, the method further comprising positioning, with the integrated interface, the stream collection opening relative to the urethral opening and engaging an interior of the vaginal opening with the probe guide passage to provide substantially simultaneous isolated passages respectively for passing a urine stream via the spillway to the urine sensing device in one of the isolated passages, and for positioning the sounding probe in the predetermined position through another of the isolated passages.

15. The method of claim 14, further comprising substantially simultaneously directing passage of urine stream past the urine sensing device via the spillway in the one of the isolated passages and positioning the sounding probe in the predetermined position through the other isolated passage to sound a predetermined anatomical region coincident with passage of the urine stream.

16. The method of claim 10, further comprising a coupling connected to the discharge opening configured for coupling the urine sensing device to the discharge opening.

17. The method of claim 10, wherein the discharge opening is configured so as to define a coupling sized and shaped so as to conformally couple an entry port of the urine sensing device to the female urinary diagnostic device, so that the urine sensing device is dependent from the female urinary diagnostic device, and the female urinary diagnostic device and urine sensing device form an assembled unit.

18. The method of claim 10, further comprising engaging the sounding probe with a coupling disposed in the probe guide passage and clamping the sounding probe to the diagnostic device so that the diagnostic device and sounding probe form an assembled unit.

\* \* \* \* \*